United States Patent
Yerkes et al.

(10) Patent No.: US 8,871,680 B2
(45) Date of Patent: Oct. 28, 2014

(54) HERBICIDAL COMPOSITIONS COMPRISING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND A DI-METHOXY-PYRIMIDINE AND DERIVATIVES THEREOF

(71) Applicant: Dow AgroSciences LLC, Indianapolis, IN (US)

(72) Inventors: Carla N. Yerkes, Crawfordsville, IN (US); Richard K. Mann, Franklin, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/833,362

(22) Filed: Mar. 15, 2013

(65) Prior Publication Data
US 2014/0031211 A1   Jan. 30, 2014

Related U.S. Application Data

(60) Provisional application No. 61/675,109, filed on Jul. 24, 2012, provisional application No. 61/675,117, filed on Jul. 24, 2012.

(51) Int. Cl.
| | |
|---|---|
| A01N 25/26 | (2006.01) |
| A01N 43/40 | (2006.01) |
| A01N 43/60 | (2006.01) |
| A01N 43/54 | (2006.01) |

(52) U.S. Cl.
CPC ............... *A01N 43/54* (2013.01); *A01N 43/40* (2013.01)
USPC ........................ 504/100; 504/130; 504/136

(58) Field of Classification Search
CPC .................................................... A01N 43/40
See application file for complete search history.

(56) References Cited

U.S. PATENT DOCUMENTS

| | | | | |
|---|---|---|---|---|
| 7,314,849 B2 * | 1/2008 | Balko et al. | | 504/244 |
| 7,622,641 B2 * | 11/2009 | McCutchen et al. | | 800/300 |
| 2009/0062121 A1 | 3/2009 | Satchivi et al. | | |
| 2010/0137137 A1 | 6/2010 | Rosinger et al. | | |
| 2011/0082162 A1 * | 4/2011 | Lorsbach et al. | | 514/274 |
| 2011/0207607 A1 * | 8/2011 | Satchivi et al. | | 504/105 |
| 2012/0115727 A1 | 5/2012 | Satchivi et al. | | |
| 2012/0190551 A1 * | 7/2012 | Yerkes et al. | | 504/242 |
| 2013/0109569 A1 | 5/2013 | Dave | | |
| 2013/0310256 A1 * | 11/2013 | Yerkes et al. | | 504/103 |
| 2014/0031210 A1 * | 1/2014 | Yerkes et al. | | 504/103 |
| 2014/0031212 A1 * | 1/2014 | Yerkes et al. | | 504/103 |
| 2014/0031213 A1 * | 1/2014 | Yerkes et al. | | 504/103 |
| 2014/0031214 A1 * | 1/2014 | Yerkes et al. | | 504/103 |
| 2014/0031215 A1 * | 1/2014 | Yerkes et al. | | 504/103 |
| 2014/0031216 A1 * | 1/2014 | Yerkes et al. | | 504/103 |
| 2014/0031217 A1 * | 1/2014 | Yerkes et al. | | 504/103 |
| 2014/0031218 A1 * | 1/2014 | Mann et al. | | 504/103 |
| 2014/0031219 A1 * | 1/2014 | Yerkes et al. | | 504/103 |
| 2014/0031220 A1 * | 1/2014 | Yerkes et al. | | 504/103 |
| 2014/0031221 A1 * | 1/2014 | Yerkes et al. | | 504/103 |
| 2014/0031222 A1 * | 1/2014 | Yerkes et al. | | 504/103 |
| 2014/0031227 A1 * | 1/2014 | Yerkes et al. | | 504/128 |
| 2014/0031228 A1 * | 1/2014 | Mann et al. | | 504/130 |
| 2014/0031229 A1 * | 1/2014 | Mann et al. | | 504/136 |

FOREIGN PATENT DOCUMENTS

WO   WO-2007082098   *   7/2007

OTHER PUBLICATIONS

Synthesis of Esters: Esterification Reactions, obtained via google.com in U.S. Appl. No. 13/840,306, obtained online Mar. 8, 2014.*
Chui, M.P., Non-Final Office Action in U.S. Appl. No. 13/840,306, Mar. 13, 2014, pp. 1-12, USPTO.*
Pryor, A.N., Notice of Allowance and Fee(s) Due for U.S. Appl. No. 13/832,978, Apr. 9, 2014, pp. 1-13, USPTO.*
Pryor, A.N., Notice of Allowance and Fee(s) Due for U.S. Appl. No. 13/833,315, Jun. 25, 2014, pp. 1-2, USPTO.*
Pryor, A.N., Notice of Allowance and Fee(s) Due for U.S. Appl. No. 13/833,315, May 12, 2014, pp. 1-8, USPTO.*

(Continued)

*Primary Examiner* — Alton Pryor
(74) *Attorney, Agent, or Firm* — Robert Chang; Faegre Baker Daniels LLP

(57) ABSTRACT

A synergistic herbicidal composition containing (a) a compound of formula (I):

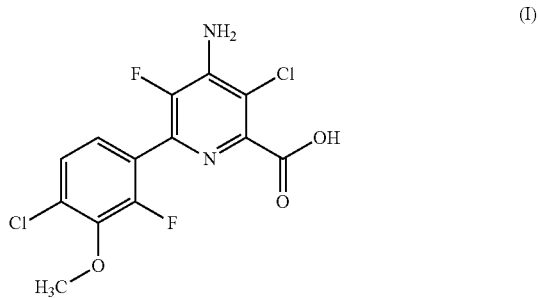

or an agriculturally acceptable salt or ester thereof and (b) dimethoxy-pyrimidine acids, including but not limited to bispyribac-sodium, pyribenzoxim, pyriftalid, pyriminobac-methyl and pyrimisulfan provide synergistic weed control of undesirable vegetation e.g., in direct-seeded, water-seeded, and transplanted rice, cereals, wheat, barley, oats, rye, sorghum, corn or maize, sugarcane, sunflower, oilseed rape, canola, sugar beet, soybean, cotton, pineapple, vegetables, pastures, grasslands, rangelands, fallowland, turf, tree and vine orchards, aquatics, plantation crops, industrial vegetation management (IVM) or rights of way (ROW).

17 Claims, No Drawings

(56) References Cited

OTHER PUBLICATIONS

Pryor, A.N., Notice of Allowance and Fee(s) Due for U.S. Appl. No. 13/833,315, Mar. 20, 2014, pp. 1-11, USPTO.*
Pryor, A.N., Notice of Allowance and Fee(s) Due for U.S. Appl. No. 13/833,372, May 14, 2014, pp. 1-8, USPTO.*
Pryor, A.N., Notice of Allowance and Fee(s) Due for U.S. Appl. No. 13/833,659, Mar. 17, 2014, pp. 1-12, USPTO.*
Pryor, A.N., Notice of Allowance and Fee(s) Due for U.S. Appl. No. 13/840,488, May 2, 2014, pp. 1-8, USPTO.*
Pryor, A.N., Notice of Allowance and Fee(s) Due for U.S. Appl. No. 13/833,965, Apr. 1, 2014, pp. 1-8, USPTO.*
Pryor, A.N., Notice of Allowance and Fee(s) Due for U.S. Appl. No. 13/834,326, May 13, 2014, pp. 1-4, USPTO.*
Pryor, A.N., Notice of Allowance and Fee(s) Due for U.S. Appl. No. 13/834,326, Apr. 2, 2014, pp. 1-9, USPTO.*
Pryor, A.N., Notice of Allowance and Fee(s) Due for U.S. Appl. No. 13/836,653, Apr. 2, 2014, pp. 1-8, USPTO.*
Pryor, A.N., Notice of Allowance and Fee(s) Due for U.S. Appl. No. 13/836,653, Jun. 17, 2014, pp. 1-5, USPTO.*
Pryor, A.N., Notice of Allowance and Fee(s) Due for U.S. Appl. No. 13/836,653, Jul. 16, 2014, pp. 1-5, USPTO.*
Pryor, A.N., Notice of Allowance and Fee(s) Due for U.S. Appl. No. 13/837,990, Apr. 1, 2014, pp. 1-8, USPTO.*
Pryor, A.N., Notice of Allowance and Fee(s) Due for U.S. Appl. No. 13/839,043, May 27, 2014, pp. 1-5, USPTO.*
Pryor, A.N., Notice of Allowance and Fee(s) Due for U.S. Appl. No. 13/839,043, Mar. 24, 2014, pp. 1-8, USPTO.*
Pryor, A.N., Notice of Allowance and Fee(s) Due for U.S. Appl. No. 13/839,043, Jun. 27, 2014, pp. 1-2, USPTO.*
Pryor, A.N., Notice of Allowance and Fee(s) Due for U.S. Appl. No. 13/840,303, Apr. 25, 2014, pp. 1-8, USPTO.*
Pryor, A.N., Notice of Allowance and Fee(s) Due for U.S. Appl. No. 13/834,706, Mar. 12, 2014, pp. 1-13, USPTO.*
Pryor, A.N., Notice of Allowance and Fee(s) Due for U.S. Appl. No. 13/834,706, Jul. 9, 2014, pp. 1-7, USPTO.*
Pryor, A.N., Notice of Allowance and Fee(s) Due for U.S. Appl. No. 13/833,923, May 2, 2014, pp. 1-9, USPTO.*
Pryor, A.N., Notice of Allowance and Fee(s) Due for U.S. Appl. No. 13/840,419, May 5, 2014, pp. 1-8, USPTO.*
Pryor, A.N., Notice of Allowance and Fee(s) Due for U.S. Appl. No. 13/840,419, Jun. 25,12, 2014, pp. 1-2, USPTO.*
Pryor, A.N., Notice of Allowance and Fee(s) Due for U.S. Appl. No. 13/840,236, Apr. 25, 2014, pp. 1-8, USPTO.*
Pryor, A.N., Notice of Allowance and Fee(s) Due for U.S. Appl. No. 13/840,346, Jun. 4, 2014, pp. 1-8, USPTO.*
Thomas, S., Written Opinion of the International Search Authority for PCT/US2013/051322, Dec. 6, 2013, pp. 1-5, ISA/US.
Thomas, S., International Search Report for PCT/US2013/051322, Dec. 6, 2013, pp. 1-4, ISA/US.

* cited by examiner

HERBICIDAL COMPOSITIONS COMPRISING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND A DI-METHOXY-PYRIMIDINE AND DERIVATIVES THEREOF

PRIORITY CLAIM

This application claims the benefit of U.S. provisional patent application Nos. 61/675,109 filed on Jul. 24, 2012 and 61/675,117 filed on Jul. 24, 2012, each of these provisional applications is incorporated herein by reference in its entirety.

FIELD

Provided herein are herbicidal compositions comprising (a) 4-amino-3-chloro-5-fluoro-6-(4-chloro-2-fluoro-3-methoxyphenyl)pyridine-2-carboxylic acid or an agriculturally acceptable ester or salt thereof and (b) a dimethoxy pyrimidine, such as a pyrimidinyloxybenzoic acid or a pyrimidinylthiobenzoic acid or agriculturally acceptable salt or esters thereof.

Provided herein are also methods of controlling undesirable vegetation comprising applying (a) 4-amino-3-chloro-5-fluoro-6-(4-chloro-2-fluoro-3-methoxyphenyl)pyridine-2-carboxylic acid or an agriculturally acceptable ester or salt thereof and (b) a dimethoxy pyrimidine, such as pyrimidinyloxybenzoic acids or pyrimidinylthiobenzoic acids or agriculturally acceptable salts or esters thereof.

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. However, there remains a need for compositions and methods that are effective in controlling undesirable vegetation.

SUMMARY

A first embodiment of the invention provided herein includes herbicidal compositions comprising an herbicidally effective amount of (a) a compound of the formula (I)

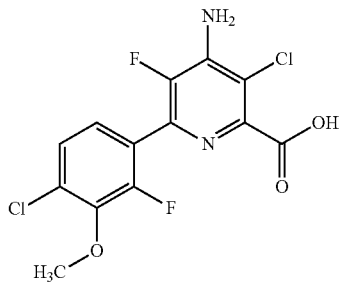

(I)

or an agriculturally acceptable salt or ester thereof, and (b) at least one a dimethoxy-pyrimidine selected from the group consisting of: pyrimidinyloxybenzoic acids, pyrmidinylthiobenzoic acids, and agriculturally acceptable salts and esters thereof.

A second embodiment includes the mixture of the first embodiment in which formula (I) is present in at least one of the following forms: a carboxylic acid, a carboxylate salt, an aralkyl, an alkyl ester, an unsubstituted benzyl, a substituted benzyl, a $C_1$-$C_4$ alkyl, and/or an n-butyl ester.

A third embodiment includes the mixture according to either the first or second embodiments wherein (b) is at least one dimethoxy-pyrimidine selected from the group consisting of: bispyribac-sodium, pyribenzoxim, pyriftalid, pyriminobac-methyl or pyrimisulfan, or an agriculturally acceptable salt, carboxylic acid, carboxylate salt, or ester thereof of at least one of the aforementioned dimethoxy-pyrimidines.

A fourth embodiment includes the mixtures according to any of the first, second, or third embodiments in which the dimethoxy-pyrimidine in the mixture is bispyribac-sodium wherein the weight ratio of the compound of formula (I) to bispyribac-sodium given in units of gae/ha to gai/ha or gae/ha to gae/ha is selected from the group of ranges of ratios and ratios consisting of about: 1:75 to 43:1, 1:0.8, 1:0.4, 1:1.6, 1:1.4, 1:0.6, 1:0.3, 1:2.3, 1:1.1, 1:4.6, 1.75:1, and 10:1 to 1:9, or within any range defined between any pair of the foregoing values.

A fifth embodiment includes the mixtures according to any of the first, second, or third embodiments in which the dimethoxy-pyrimidine in the mixture is pyribenzoxim wherein the weight ratio of the compound of formula (I) to pyribenzoxim given in units of gae/ha to gai/ha or gae/ha to gae/ha is selected from the group of ranges of ratios and ratios consisting of about: 2:45 to 10:1, 1:8.8, 1:4.4, 1:9, and 1:45, or within any range defined between any pair of the foregoing values.

A sixth embodiment includes the mixtures according to any of the first, second, or third embodiments in which the dimethoxy-pyrimidine in the mixture is pyriftalid wherein the weight ratio of the compound of formula (I) to pyriftalid given in units of gae/ha to gai/ha or gae/ha to gae/ha is selected from the group of ranges of ratios and ratios consisting of about: 1:150 to 3:1, 1:10, 1:21, 1:2.6, 1:5.2, 1:2.5, 1:26, 1:10.3, 1:6, 1:21, or within any range defined between any pair of the foregoing values.

A seventh embodiment includes the mixtures according to any of the first, second, or third embodiments in which the dimethoxy-pyrimidine in the mixture is pyriminobac-methyl wherein the weight ratio of the compound of formula (I) to pyriminobac-methyl given in units of gae/ha to gai/ha or gae/ha to gae/ha is selected from the group of ranges of ratios and ratios consisting of about: 1:45 to 27:1, 1:9, and 1:4.4, or within any range defined between any pair of the foregoing values.

An eighth embodiment includes the mixtures according to any of the first, second, or third embodiments in which the dimethoxy-pyrimidine in the mixture is pyrimisulfan wherein the weight ratio of the compound of formula (I) to pyrimisulfan given in units of gae/ha to gai/ha or gae/ha to gae/ha is selected from the group of ranges of ratios and ratios consisting of about: 1:100 to 30:1, 1:20 to 20:1, and 1:1 to 10:1, or within any range defined between any pair of the foregoing values.

A ninth embodiment includes any composition according to any of the first through the eighth embodiments wherein the mixture further comprises at least one an agriculturally acceptable agent selected from the group consisting of an adjuvant, a carrier, or a safener.

A tenth embodiment includes methods of controlling undesirable vegetation comprising the steps of applying or otherwise contacting vegetation and/or soil, and/or water with an herbicidally effective amount of at least one mixture according to any of the first through the ninth embodiments.

An eleventh embodiment includes methods according to the tenth embodiment wherein undesirable vegetation is controlled by practicing at least one of the methods in at least one member of the group consisting of: direct-seeded, water-seeded, and/or transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM), or rights-of-way (ROW).

A twelfth embodiment includes methods according to either of the tenth and eleventh embodiments wherein an herbicidally effective amount of the mixture is applied either pre- or post emergently to at least one of the following: a crop, a field, a ROW, or a rice paddy.

A thirteenth embodiment includes methods according to any of the tenth through the twelfth embodiments wherein the undesirable vegetation may be controlled by practicing at least one of the methods on at least one plant that is resistant or tolerant to the members of the group consisting of: glyphosate-, 5-enolpyruvylshikimate-3-phosphate (EPSP) synthase inhibitor-, glufosinate-, glutamine synthetase inhibitor-, dicamba-, phenoxy auxin-, pyridyloxy auxin-, synthetic auxin-, auxin transport inhibitor-, aryloxyphenoxypropionate-, cyclohexanedione-, phenylpyrazoline-, acetyl CoA carboxylase (ACCase) inhibitor-, imidazolinone-, sulfonylurea-, pyrimidinylthiobenzoate-, triazolopyrimidine-, sulfonylaminocarbonyltriazolinone-, acetolactate synthase (ALS) or acetohydroxy acid synthase (AHAS) inhibitor-, 4-hydroxyphenyl-pyruvate dioxygenase (HPPD) inhibitor-, phytoene desaturase inhibitor-, carotenoid biosynthesis inhibitor-, protoporphyrinogen oxidase (PPO) inhibitor-, cellulose biosynthesis inhibitor-, mitosis inhibitor-, microtubule inhibitor-, very long chain fatty acid inhibitor-, fatty acid and lipid biosynthesis inhibitor-, photosystem I inhibitor-, photosystem II inhibitor-, protoporphyrinogen oxidase (PPO) inhibitor-, triazine-, and bromoxynil.

A fourteenth embodiment includes a at least one method according to any of the tenth through the thirteenth embodiments wherein a plant that is resistant or tolerant to at least one herbicide is treated, and where the resistant or tolerant crop possesses multiple or stacked traits conferring tolerance to multiple herbicides or inhibitors of multiple herbicide modes of action, in some embodiments the treated plant that expresses resistance to an herbicide is a itself undesirable vegetation.

A fifteenth embodiment includes methods according to the fourteenth embodiment, wherein the resistant or tolerant weed is a biotype with resistance or tolerance to multiple herbicides, multiple chemical classes, inhibitors of multiple herbicide modes-of-action, or via multiple resistance mechanisms.

A sixteenth embodiment includes at least one of the methods according to either the fourteenth or fifteenth embodiments, wherein the resistant or tolerant undesirable plant is a biotype resistant or tolerant to at least one or more compounds that act according to at least one mode of action selected from the group consisting of: acetolactate synthase (ALS) inhibitors or acetohydroxy acid synthase (AHAS), photosystem II inhibitors, acetyl CoA carboxylase (ACCase) inhibitors, synthetic auxins, auxin transport inhibitors, photosystem I inhibitors, 5-enolpyruvylshikimate-3-phosphate (EPSP) synthase inhibitors, microtubule assembly inhibitors, fatty acid and lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action, quinclorac, arylaminopropionic acids, difenzoquat, endothall, or organoarsenicals.

A seventeenth embodiment includes methods of controlling undesirable vegetation comprising the step of applying an herbicidally effective amount of at least one mixture according to the fourth embodiment wherein the amount of the mixture is applied at a rate, expressed in gai/ha or gae/ha of bispyribac-sodium selected from the group of rates and ranges of rates consisting of, about: 1, 5, 7, 10, 14, 20, 40, 80, and 100, or within any range defined between any pair of the foregoing values.

An eighteenth embodiment includes methods according to either of the fourth and sixteenth embodiments wherein the controlled plant is at least one plant selected from the group consisting of: LEFCH, ECHCG, ECHOR, SCPMA, and CYPRO, still other embodiments include controlling plants from the genera consisting of: *Leptochloa, Echinochloa, Bolboschoenus*, and *Cyperus*.

An nineteenth embodiment includes methods of controlling undesirable vegetation comprising the step of applying an herbicidally effective amount of at least one a mixture according to the fifth embodiment wherein the amount of the mixture is applied at a rate, expressed in gai/ha or gae/ha of pyribenzoxim selected from the group of rates and ranges of rates consisting of, about: 70, 15 to 60, and 2 to 300, or within any range defined between any pair of the foregoing values.

A twentieth embodiment includes methods according to either of the fifth and nineteenth embodiments wherein the controlled plant is at least one plant selected from the group consisting of: ECHCG, still other embodiments include controlling plants from the genera consisting of: *Echinochloa*.

A twenty-first embodiment includes methods of controlling undesirable vegetation comprising the step of applying an herbicidally effective amount of at least one a mixture according to the sixth embodiment wherein the amount of the mixture is applied at a rate, expressed in gai/ha or gae/ha of pyriftalid selected from the group of rates and ranges of rates consisting of, about: 1:150 to 3:1, 1:10.3, 1:21, 1:2.6, 1:5.2, and 1:2.5, or within any range defined between any pair of the foregoing values.

A twenty-second embodiment includes methods according to either of the sixth and twenty-second embodiments wherein the controlled plant is at least one plant selected from the group consisting of: BRAPP, LEFCH, CYPRO and FIMMI, still other embodiments include controlling plants from the genera consisting of: *Leptochloa, Cyperus, Fimbristylis* and *Brachiaria*.

A twenty-third embodiment includes methods of controlling undesirable vegetation comprising the step of applying an herbicidally effective amount of at least one a mixture according to the seventh embodiment wherein the amount of the mixture is applied at a rate, expressed in gai/ha or gae/ha of pyriminobac-methyl selected from the group of rates and ranges of rates consisting of, about: 1:45 to 27:1, 11.25, 22.5, 45, 90, 180, or within any range defined between any pair of the foregoing values.

A twenty-fourth embodiment includes methods according to either of the seventh and twenty-third embodiments wherein the controlled plant is at least one plant selected from the group consisting of: DIGSA, IPOHE, LEFCH, ECHCO, FIMMI, SCPMA and CYPRO, still other embodiments include controlling plants from the genera consisting of: *Digitaria, Ipomoea, Leptochloa, Echinochloa, Fimbristylis, Bolboschoenus* and *Cyperus*.

A twenty-fifth embodiment includes methods of controlling undesirable vegetation comprising the step of applying an herbicidally effective amount of at least one a mixture according to the seventh embodiment wherein the amount of the mixture is applied at a rate, expressed in gai/ha or gae/ha of pyrimisulfan selected from the group of rates and ranges of rates consisting of, about: 5, 20, 50, 100, 150, 200, and 300, or within any range defined between any pair of the foregoing values.

A twenty-sixth embodiment includes methods according to either of the seventh and twenty-fifth embodiments wherein the controlled plant is at least one plant selected from the group consisting of: CYPRO, ECHCG, ECHCO, LEFCH, SCPMA, DIGSA, IPOHE, and FIMMI, still other embodiments include controlling plants from the genera consisting of: *Cyperus, Digitaria, Echinochloa, Fimbristylis, Ipomoea, Leptochloa, Schoenoplectus,* and *Bolboschoenus.*

Provided herein are herbicidal compositions comprising an herbicidally effective amount of (a) a compound of the formula (I)

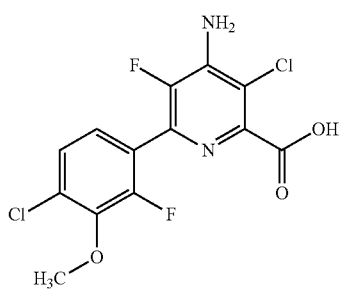

(I)

or an agriculturally acceptable salt or ester of thereof, and (b) a synthetic auxin herbicide. The compositions may also include an agriculturally acceptable adjuvant or carrier.

Provided herein are also methods of controlling undesirable vegetation comprising applying (a) a compound of formula (I) or an agriculturally acceptable ester or salt thereof and (b) a synthetic auxin herbicide or an agriculturally acceptable salt or ester thereof.

DETAILED DESCRIPTION

Definitions

As used herein, the compound of formula (I) has the following structure:

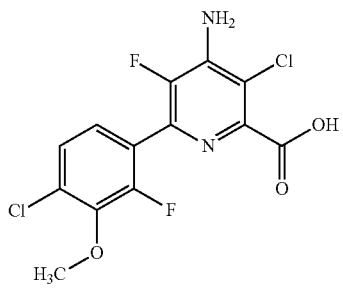

(I)

The compound of formula (I) can be identified by the name 4-amino-3-chloro-6-(4-chloro-2-fluoro-3-methoxyphenyl)-5-fluoropyridine-2-carboxylic acid and has been described in U.S. Pat. No. 7,314,849 (B2), which is incorporated herein by reference in its entirety. Exemplary uses of the compound of the formula (I) include controlling undesirable vegetation, including grass, broadleaf and sedge weeds, in multiple non-crop and cropping situations.

Pyrimidineoxycarboxylic acids contain in certain embodiments the following core structure:

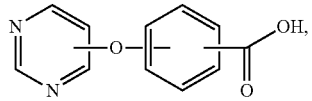

which can be substituted with one or more substituents, and salts and esters thereof. The phenyl and pyrimidine may independently be part of a multicyclic ring system. The oxygen connected to both the pyrimidine and phenyl may be replaced with another heteroatom, e.g., S. Without being limited to any theory, the compounds inhibit acetolactate synthase (ALS) or (AHAS) acetohydroxyacid synthase (AHAS), the first common enzyme in the biosynthesis of the branched chain amino acids.

Exemplary pyrimidinylthiobenzoate acids or salts or esters thereof include, but are not limited to bispyribac-sodium, pyribenzoxim, pyriftalid, pyriminobac-methyl and pyrimisulfan, agriculturally acceptable derivatives, e.g., carboxylic acid, carboxylate salt, or ester thereof.

As used herein, bispyribac-sodium is sodium 2,6-bis[(4,6-dimethoxy-2-pyrimidinyl)oxy]benzoate and possesses the following structure:

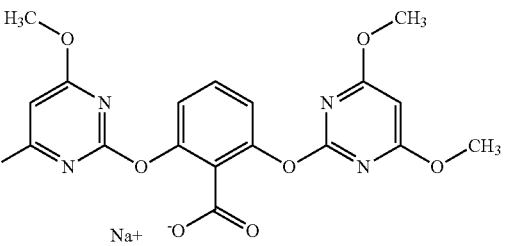

The compound has been described in Tomlin, C., ed. A World Compendium The Pesticide Manual. 15$^{th}$ ed. Alton: BCPC Publications, 2009 (hereafter "*The Pesticide Manual*, Fifteenth Edition, 2009."). Exemplary uses of bispyribac-sodium include its use to control grasses, sedges and broadleaf weeds, e.g., in direct-seeded and water-seeded rice and in turf.

As used herein, pyribenzoxim is diphenylmethanone O-[2,6-bis[(4,6-dimethoxy-2-pyrimidinyl)oxy]benzoyl]oxime and possesses the following structure:

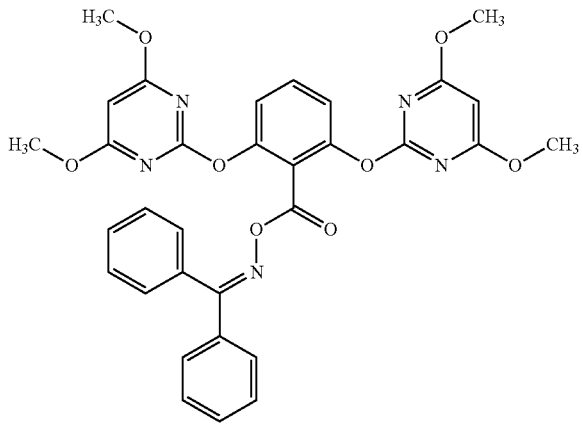

The compound is described in *The Pesticide Manual*, Fifteenth Edition, 2009. Exemplary uses of pyribenzoxim include its use for post-emergence control of barnyard grass, blackgrass and polygonums, e.g., in rice, wheat and zoysia-grass.

As used herein, pyriftalid is 7-[(4,6-dimethoxy-2-pyrimidinyl)thio]-3-methyl-1 (3H)-isobenzofuranone and possesses the following structure:

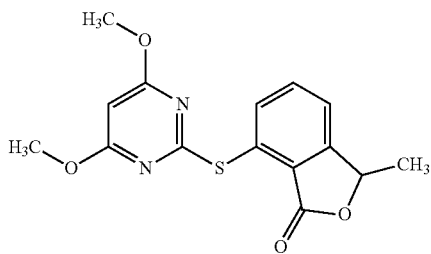

in the compound is described in *The Pesticide Manual*, Fifteenth Edition, 2009. Exemplary uses of pyriftalid include its use for post-emergence, broad-spectrum control of weed, e.g., in rice.

As used herein, pyriminobac-methyl is methyl 2-[(4,6-dimethoxy-2-pyrimidinyl)oxy]-6-[1-(methoxyimino)ethyl] benzoate and possesses the following structure:

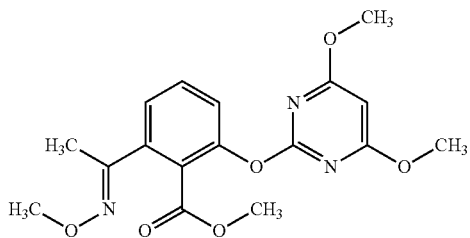

The compound is described in *The Pesticide Manual*, Fifteenth Edition, 2009. Exemplary uses of pyriminobac-methyl include its use for early post-emergence control of barnyard grass, e.g., in paddy rice.

As used herein, pyrimisulfan is N-[2-[(4,6-dimethoxy-2-pyrimidinyl)hydroxymethyl]-6-(methoxymethyl)phenyl]-1,1-difluoromethanesulfonamide and possesses the following structure:

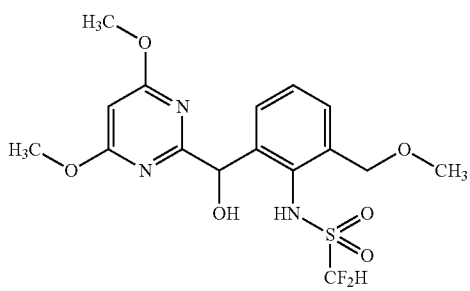

Its herbicidal activity is exemplified in the Journal of Pesticide Science (Tokyo, Japan) (2012), 37(1), 62-68. Pyrimisulfan can be used, e.g., as an herbicide for the control of rice weeds in rice fields. As used herein, herbicide means a compound, e.g., active ingredient that kills, controls or otherwise adversely modifies the growth of plants.

As used herein, an herbicidally effective or vegetation controlling amount is an amount of active ingredient which causes an adversely modifying effect to the vegetation e.g., causing deviations from natural development, killing, effecting regulation, causing desiccation, causing retardation, and the like.

As used herein, controlling undesirable vegetation means preventing, reducing, killing, or otherwise adversely modifying the development of plants and vegetation. Described herein are methods of controlling undesirable vegetation through the application of certain herbicide combinations or compositions. Methods of application include, but are not limited to applications to the vegetation or locus thereof, e.g., application to the area adjacent to the vegetation, as well as pre-emergence, post-emergence, foliar (broadcast, directed, banded, spot, mechanical, over-the-top, or rescue), and in-water applications (emerged and submerged vegetation, broadcast, spot, mechanical, water-injected, granular broadcast, granular spot, shaker bottle, or stream spray) via hand, backpack, machine, tractor, or aerial (airplane and helicopter) application methods.

As used herein, plants and vegetation include, but are not limited to, germinant seeds, emerging seedlings, plants emerging from vegetative propagules, immature vegetation, and established vegetation.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can be hydrolyzed, oxidized, metabolized, or otherwise converted, e.g., in plants, water, or soil, to the corresponding carboxylic acid which, depending on the pH, may be in the dissociated or undissociated form.

Exemplary salts include those derived from alkali or alkaline earth metals and those derived from ammonia and amines Exemplary cations include sodium, potassium, magnesium, and aminium cations of the formula:

$R^1R^2R^3R^4N^+$ wherein $R^1$, $R^2$, $R^3$ and $R^4$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC)

or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

Compositions and Methods

Provided herein are herbicidal compositions comprising an herbicidally effective amount of (a) a compound of the formula (I)

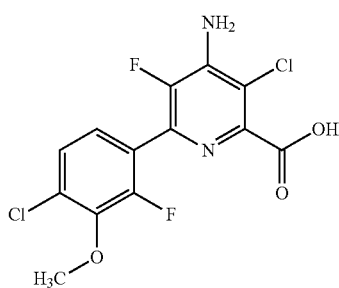

or an agriculturally acceptable salt or ester of thereof, and (b) a pyrimidinylthiobenzoate acid or agriculturally acceptable salt or ester thereof.

Provided herein are also methods of controlling undesirable vegetation comprising contacting the vegetation or the locus thereof, i.e., the area adjacent to the vegetation, with or applying to the soil or water to prevent the emergence or growth of vegetation an herbicidally effective amount of the compound of formula (I) or agriculturally acceptable salt or ester thereof and (b) a pyrimidinylthiobenzoate acid. In certain embodiments, the methods employ the compositions described herein.

Furthermore, in some embodiments, the combination of compound (I) or agriculturally acceptable salt or ester thereof and pyrimidinylthiobenzoate acids, or an agriculturally acceptable salt or ester thereof exhibits synergism, e.g., the herbicidal active ingredients are more effective in combination than when applied individually. Synergism has been defined as "an interaction of two or more factors such that the effect when combined is greater than the predicted effect based on the response of each factor applied separately." Senseman, S., ed. Herbicide Handbook. 9th ed. Lawrence: Weed Science Society of America, 2007. In certain embodiments, the compositions exhibit synergy as determined by the Colby's equation. Colby, S. R. 1967. Calculation of the synergistic and antagonistic response of herbicide combinations. Weeds 15:20-22.

In certain embodiments of the compositions and methods described herein, the compound of formula (I), i.e., the carboxylic acid, is employed. In certain embodiments, a carboxylate salt of the compound of formula (I) is employed. In certain embodiments, an aralkyl or alkyl ester is employed. In certain embodiments, a benzyl, substituted benzyl, or $C_{1-4}$ alkyl, e.g., n-butyl ester is employed. In certain embodiments, the benzyl ester is employed.

In certain embodiments, the pyrimidinylthiobenzoate acid is bispyribac-sodium, pyribenzoxim, pyriftalid, pyriminobac-methyl or pyrimisulfan or an agriculturally acceptable derivative thereof.

In some embodiments, the compound of formula (I) or salt or ester thereof and bispyribac sodium, pyribenzoxim, pyriftalid, pyriminobac-methyl and pyrimisulfan or an agriculturally acceptable salt or ester thereof, are formulated in one composition, tank mixed, applied simultaneously, or applied sequentially.

Herbicidal activity is exhibited by the compounds when they are applied directly to the plant or to the locus of the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. In some embodiments, the compositions described herein are applied as a post-emergence application, pre-emergence application, or in-water application to flooded paddy rice or water bodies (e.g., ponds, lakes and streams), to relatively immature undesirable vegetation to achieve the maximum control of weeds.

In some embodiments, the compositions and methods provided herein are utilized to control weeds in crops, including but not limited to direct-seeded, water-seeded and transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM) and rights of way (ROW).

In certain embodiments, the compositions and methods provided herein are utilized to control weeds in rice. In certain embodiments, the rice is direct-seeded, water-seeded, or transplanted rice.

The compositions and methods described herein can be used to control undesirable vegetation in glyphosate-tolerant-, 5-enolpyruvylshikimate-3-phosphate (EPSP) synthase inhibitor-tolerant-, glufosinate-tolerant-, glutamine synthetase inhibitor-tolerant-, dicamba-tolerant-, phenoxy auxin-tolerant-, pyridyloxy auxin-tolerant-, auxin-tolerant-, auxin transport inhibitor-tolerant-, aryloxyphenoxypropionate-tolerant-, cyclohexanedione-tolerant-, phenylpyrazoline-tolerant-, acetyl CoA carboxylase (ACCase) inhibitor-tolerant-, imidazolinone-tolerant-, sulfonylurea-tolerant-, pyrimidinylthiobenzoate-tolerant-, triazolopyrimidine-tolerant-, sulfonylaminocarbonyltriazolinone-tolerant-, acetolactate synthase (ALS) or acetohydroxy acid synthase (AHAS) inhibitor-tolerant-, 4-hydroxyphenyl-pyruvate dioxygenase (HPPD) inhibitor-tolerant-, phytoene desaturase inhibitor-tolerant-, carotenoid biosynthesis inhibitor-tolerant-, protoporphyrinogen oxidase (PPO) inhibitor-tolerant-, cellulose biosynthesis inhibitor-tolerant-, mitosis inhibitor-tolerant-, microtubule inhibitor-tolerant-, very long chain fatty acid inhibitor-tolerant-, fatty acid and lipid biosynthesis inhibitor-tolerant-, photosystem I inhibitor-tolerant-, photosystem II inhibitor-tolerant-, triazine-tolerant- and bromoxynil-tolerant-crops (such as, but not limited to, soybean, cotton, canola/oilseed rape, rice, cereals, corn, sorghum, sunflower, sugar beet, sugarcane, turf, etc), for example, in conjunction with glyphosate, EPSP synthase inhibitors, glufosinate, glutamine synthase inhibitors, dicamba, phenoxy auxins, pyridyloxy auxins, synthetic auxins, auxin transport inhibitors, aryloxyphenoxypropionates, cyclohexanediones, phenylpyrazolines, ACCase inhibitors, imidazolinones, sulfonylureas, pyrimidinylthiobenzoates, triazolopyrimidines, sulfonylaminocarbonyltriazolinones, ALS or AHAS inhibitors, HPPD inhibitors, phytoene desaturase inhibitors, carotenoid biosynthesis inhibitors, PPO inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil. The compositions and methods may be used in controlling undesirable vegetation in crops possessing multiple or stacked traits conferring tolerance to multiple chemistries and/or inhibitors of multiple modes of action. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation, as a tank mix or sequentially.

The compositions and methods may be used in controlling undesirable vegetation in crops possessing agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture).

The compositions and methods provided herein are utilized to control undesirable vegetation. Undesirable vegetation includes, but is not limited to, undesirable vegetation that occurs in rice, cereals, wheat, barley, oats, rye, range and pasture, fallowland, row crops (e.g., corn/maize, sugarcane, sunflower, oilseed rape, canola, sugar beet, soybean, cotton), turf, tree and vine orchards, plantation crops, vegetables, and ornamental species, aquatic or non-crop settings, (e.g., rights-of-way, industrial vegetation management).

In some embodiments, the methods provided herein are utilized to control undesirable vegetation in rice. In certain embodiments, the undesirable vegetation is *Brachiaria platyphylla* (Groseb.) Nash or *Urochloa platyphylla* (Nash) R. D. Webster (broadleaf signalgrass, BRAPP), *Digitaria sanguinalis* (L.) Scop. (large crabgrass, DIGSA), *Echinochloa* species (ECHSS), *Echinochloa crus-galli* (L.) P. Beauv. (barnyardgrass, ECHCG), *Echinochloa crus-pavonis* (Kunth) Schult. (gulf cockspur, ECHCV), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Echinochloa phyllopogon* (Stapf) Koso-Pol. (rice barnyardgrass, ECHPH), *Echinochloa polystachya* (Kunth) Hitchc. (creeping river grass, ECHPO), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl) Hitchc. (Amazon sprangletop, LEFPA), *Oryza* species (red and weedy rice, ORYSS), *Panicum dichotomiflorum* (L.) Michx. (fall panicum, PANDI), *Paspalum dilatatum* Poir. (dallisgrass, PASDI), *Rottboellia cochinchinensis* (Lour.) W. D. Clayton (itchgrass, ROOEX), *Cyperus* species (CYPSS), *Cyperus difformis* L. (smallflower flatsedge, CYPDI), *Cyperus dubius* Rottb. (MAPDU), *Cyperus esculentus* L. (yellow nutsedge, CYPES), *Cyperus iria* L. (rice flatsedge, CYPIR), *Cyperus rotundus* L. (purple nutsedge, CYPRO), *Cyperus serotinus* Rottb./C. B. Clarke (tidalmarsh flatsedge, CYPSE), *Eleocharis* species (ELOSS), *Fimbristylis miliacea* (L.) Vahl (globe fringerush, FIMMI), *Schoenoplectus* species (SCPSS), *Schoenoplectus juncoides* Roxb. (Japanese bulrush, SCPJU), *Bolboschoenus maritimus* (L.) Palla or, *Schoenoplectus maritimus* L. Lye (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Commelina benghalensis* L. (Benghal dayflower, COMBE), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea* species (morningglories, IPOSS), *Ipomoea hederacea* (L.) Jacq. (ivyleaf morningglory, IPOHE), *Lindernia dubia* (L.) Pennell (low false pimpernel, LIDDU), *Ludwigia* species (LUDSS), *Ludwigia linifolia* Poir. (southeastern primrose-willow, LUDLI), *Ludwigia octovalvis* (Jacq.) Raven (longfruited primrose-willow, LUDOC), *Monochoria korsakowii* Regel & Maack (monochoria, MOOKA), *Monochoria vaginalis* (Berm. F.) C. Presl ex Kuhth, (monochoria, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp sesbania, SEBEX), or *Sphenoclea zeylanica* Gaertn. (gooseweed, SPDZE).

In some embodiments, the methods provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Phalaris minor* Retz. (littleseed canarygrass, PHAMI), *Poa annua* L. (annual bluegrass, POANN), *Setaria pumila* (Poir.) Roemer & J. A. Schultes (yellow foxtail, SETLU), *Setaria viridis* (L.) Beauv. (green foxtail, SETVI), *Amaranthus retroflexus* L. (redroot pigweed, AMARE), *Brassica* species (BRSSS), *Chenopodium album* L. (common lambsquarters, CHEAL), *Cirsium arvense* (L.) Scop. (Canada thistle, CIRAR), *Galium aparine* L. (catchweed bedstraw, GALAP), *Kochia scoparia* (L.) Schrad. (kochia, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Sinapis* species (SINSS), *Sinapis arvensis* L. (wild mustard, SINAR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the methods provided herein are utilized to control undesirable vegetation in range and pasture, fallowland, IVM and ROW. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Daucus carota* L. (wild carrot, DAUCA), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly sida, SIDSP), *Sinapis arvensis* L. (wild mustard, SINAR), *Sonchus arvensis* L. (perennial sowthistle, SONAR), *Solidago* species (goldenrod, SOOSS),

*Taraxacum officinale* G. H. Weber ex Wiggers (dandelion, TAROF), *Trifolium repens* L. (white clover, TRFRE), or *Urtica dioica* L. (common nettle, URTDI).

In some embodiments, the methods provided herein are utilized to control undesirable vegetation found in row crops, tree and vine crops, and perennial crops. In certain embodiments, the undesirable vegetation is *Alopecurus myosuroides* Huds. (blackgrass, ALOMY), *Avena fatua* L. (wild oat, AVEFA), *Brachiaria decumbens* Stapf. or *Urochloa decumbens* (Stapf) R. D. Webster (Surinam grass, BRADC), *Brachiaria brizantha* (Hochst. ex A. Rich.) Stapf. or *Urochloa brizantha* (Hochst. ex A. Rich.) R. D. (beard grass, BRABR), *Brachiaria platyphylla* (Groseb.) Nash or *Urochloa platyphylla* (Nash) R. D. Webster (broadleaf signalgrass, BRAPP), *Brachiaria plantaginea* (Link) Hitchc. or *Urochloa plantaginea* (Link) R. D. Webster (alexandergrass, BRAPL), *Cenchrus echinatus* L. (southern sandbar, CENEC), *Digitaria horizontalis* Willd. (Jamaican crabgrass, DIGHO), *Digitaria insularis* (L.) Mez ex Ekman (sourgrass, TRCIN), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Eleusine indica* (L.) Gaertn. (goosegrass, ELEIN), *Lolium multiflorum* Lam. (Italian ryegrass, LOLMU), *Panicum dichotomiflorum* Michx. (fall *panicum*, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Anoda cristata* (L.) Schlecht. (spurred anoda, ANVCR), *Asclepias syriaca* L. (common milkweed, ASCSY), *Bidens pilosa* L. (hairy beggarticks, BIDPI), *Borreria* species (BOISS), *Borreria alata* (Aubl.) DC. or *Spermacoce alata* Aubl. (broadleaf buttonweed, BOILF), *Spermacose latifolia* (broadleaved button weed, BOILF), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Euphorbia hirta* L. or *Chamaesyce hirta* (L.) Millsp. (garden spurge, EPHHI), *Euphorbia dentata* Michx. (toothed spurge, EPHDE), *Erigeron bonariensis* L. or *Conyza bonariensis* (L.) Cronq. (hairy fleabane, ERIBO), *Erigeron canadensis* L. (Canadian fleabane, ERICA), *Conyza sumatrensis* (Retz.) E. H. Walker (tall fleabane, ERIFL), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Richardia* species (pusley, RCHSS), *Sida* species (sida, SIDSS), *Sida spinosa* L. (prickly sida, SIDSP), *Sinapis arvensis* L. (wild mustard, SINAR), *Solanum ptychanthum* Dunal (eastern black nightshade, SOLPT), *Tridax procumbens* L. (coat buttons, TRQPR), or *Xanthium strumarium* L. (common cocklebur, XANST. In some embodiments, the methods provided herein are utilized to control undesirable vegetation in turf In certain embodiments, the undesirable vegetation is *Bellis perennis* L. (English daisy, BELPE), *Cyperus esculentus* L. (yellow nutsedge, CYPES), *Cyperus* species (CYPSS), *Digitaria sanguinalis* (L.) Scop. (large crabgrass, DIGSA), *Diodia virginiana* L. (Virginia buttonweed, DIQVI), *Euphorbia* species (spurge, EPHSS), *Glechoma hederacea* L. (ground ivy, GLEHE), *Hydrocotyle umbellata* L. (dollarweed, HYDUM), *Kyllinga* species (*kyllinga*, KYLSS), *Lamium amplexicaule* L. (henbit, LAMAM), *Murdannia nudiflora* (L.) Brenan (doveweed, MUDNU), *Oxalis* species (woodsorrel, OXASS), *Plantago major* L. (broadleaf plantain, PLAMA), *Plantago lanceolata* L. (buckhorn/narrowleaf plantain, PLALA), *Phyllanthus urinaria* L. (chamberbitter, PYLTE), *Rumex obtusifolius* L. (broadleaf dock, RUMOB), *Stachys floridana* Shuttlew. (Florida betony, STAFL), *Stellaria media* (L.) Vill. (common chickweed, STEME), *Taraxacum officinale* G. H. Weber ex Wiggers (dandelion, TAROF), *Trifolium repens* L. (white clover, TRFRE), or *Viola* species (wild violet, VIOSS).

In some embodiments, the compositions and methods provided herein are utilized to control undesirable vegetation consisting of grass, broadleaf and sedge weeds. In certain embodiments, the compositions and methods provided herein are utilized to control undesirable vegetation including *Cyperus, Digitaria, Echinochloa, Fimbristylis, Ipomoea, Leptochloa,* and *Schoenoplectus*.

In some embodiments, the combination of compound (I) or agriculturally acceptable ester or salt thereof and bispyribac-sodium, pyribenzoxim, pyriftalid, pyriminobac-methyl and pyrimisulfan or agriculturally acceptable salt or ester thereof are used to control *Cyperus rotundus, Digitaria sanguinalis, Echinochloa crus-galli, Echinochloa colona, Fimbristylis miliacea, Ipomoea hederacea, Leptochloa chinensis,* and *Schoenoplectus maritimus* or *Bolboschoenus maritimus*.

The compounds of formula I or agriculturally acceptable salt or ester thereof may be used to control herbicide resistant or tolerant weeds. The methods employing the combination of a compound of formula I or agriculturally acceptable salt or ester thereof and the compositions described herein may also be employed to control herbicide resistant or tolerant weeds. Exemplary resistant or tolerant weeds include, but are not limited to, biotypes resistant or tolerant to acetolactate synthase (ALS) or acetohydroxy acid synthase (AHAS) inhibitors (e.g., imidazolinones, sulfonylureas, pyrimidinylthiobenzoates, triazolopyrimidines, and sulfonylaminocarbonyltriazolinones), photosystem II inhibitors (e.g., phenylcarbamates, pyridazinones, triazines, triazinones, uracils, amides, ureas, benzothiadiazinones, nitriles, phenylpyridazines), acetyl CoA carboxylase (ACCase) inhibitors (e.g., aryloxyphenoxypropionates, cyclohexanediones, phenylpyrazolines), synthetic auxins, (e.g., benzoic acids, phenoxycarboxylic acids, pyridine carboxylic acids, quinoline carboxylic acids), auxin transport inhibitors (e.g., phthalamates, semicarbazones), photosystem I inhibitors (e.g., bipyridyliums), 5-enolpyruvylshikimate-3-phosphate (EPSP) synthase inhibitors (e.g., glyphosate), glutamine synthetase inhibitors (e.g., glufosinate, bialafos), microtubule assembly inhibitors (e.g., benzamides, benzoic acids, dinitroanilines, phosphoramidates, pyridines), mitosis inhibitors (e.g., carbamates), very long chain fatty acid (VLCFA) inhibitors (e.g., acetamides, chloroacetamides, oxyacetamides, tetrazolinones), fatty acid and lipid synthesis inhibitors (e.g., phosphorodithioates, thiocarbamates, benzofuranes, chlorocarbonic acids), protoporphyrinogen oxidase (PPO) inhibitors (e.g., diphenylethers, N-phenylphthalimides, oxadiazoles, oxazolidinediones, phenylpyrazoles, pyrimidindiones, thiadiazoles, triazolinones), carotenoid biosynthesis inhibitors (e.g., clomazone, amitrole, aclonifen), phytoene desaturase (PDS) inhibitors (e.g., amides, anilidex, furanones, phenoxybutan-amides, pyridiazinones, pyridines), 4-hydroxyphenyl-pyruvate-dioxygenase (HPPD) inhibitors (e.g., callistemones, isoxazoles, pyrazoles, triketones), cellulose biosynthesis inhibitors (e.g., nitriles, benzamides, quinclorac, triazolocarboxamides), herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, biotypes with resistance or tolerance to multiple chemical classes, biotypes with resistance or tolerance to multiple herbicide modes-of-action, and biotypes with multiple resistance or tolerance mechanisms (e.g., target site resistance or metabolic resistance).

In some embodiments, an agriculturally acceptable ester or salt of compound (I) is employed. In certain embodiments, an agriculturally acceptable ester is employed. In certain embodiments, the ester is a $C_{1-4}$ alkyl ester. In certain embodiments, the ester is a n-butyl ester. In certain embodiments, the ester is a benzyl ester. In certain embodiments, compound (I), which is a carboxylic acid, is employed.

In some embodiments, an agriculturally acceptable ester or salt of bispyribac-sodium, pyribenzoxim, pyriftalid, pyriminobac-methyl and pyrimisulfan is employed in the methods or compositions described herein. In certain embodiments, the sodium salt of bispyribac is employed.

In certain embodiments of the compositions and methods described herein, the compound of formula (I) or salt or ester thereof is used in combination with bispyribac-sodium or carboxylic acid or ester thereof or other bispyribac salt. With regard to the compositions, in some embodiments, the weight ratio of the compound of formula (I) or salt or ester thereof to bispyribac-sodium or carboxylic acid or ester thereof or other bispyribac salt is within the range of from about 1:75 to about 43:1. In certain embodiments, the weight ratio of the compound of formula (I) or salt or ester thereof to bispyribac-sodium or salt or ester thereof is within the range of from about 1:9 to about 10:1. In certain embodiments, the weight ratio of the compound of formula (I) or salt or ester thereof to bispyribac-sodium or carboxylic acid or ester thereof or other bispyribac salt is within the range of from about 1:10 to about 7:1. In certain embodiments, the weight ratio of the compound of formula (I) or salt or ester thereof to bispyribac-sodium or carboxylic acid or ester thereof or other bispyribac salt is within the range of from about 1:5 to about 3.5:1. In certain embodiments, the compositions provided herein comprise the compound of formula (I) or its benzyl or n-butyl ester and bispyribac-sodium. In one embodiment, the composition comprises the compound of formula (I) and bispyribac-sodium, wherein the weight ratio of the compound of formula (I) to the bispyribac-sodium is about 1:3 to about 3.5:1. In one embodiment, the composition comprises the benzyl ester of the compound of formula (I) and bispyribac-sodium, wherein the weight ratio of the benzyl ester of the compound of formula (I) to bispyribac-sodium is about 1:5 to about 2.5:1. In one embodiment, the composition comprises the n-butyl ester of the compound of formula (I) and bispyribac-sodium, wherein the weight ratio of the n-butyl ester of the compound of formula (I) to bispyribac-sodium is about 1:1.1 to about 1.75:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 9 grams active ingredient per hectare (gai/ha) to about 450 gai/ha based on the total amount of active ingredients in the composition. In certain embodiments, the composition is applied at an application rate of from about 12 grams active ingredient per hectare (gai/ha) to about 110 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and bispyribac-sodium or carboxylic acid or ester thereof or other bispyribac salt, e.g., sequentially or simultaneously. In some embodiments, the bispyribac-sodium or carboxylic acid or ester thereof or other bispyribac salt is applied at a rate from about 7 gai/ha to about 150 gai/ha and the compound of formula (I) of salt or ester thereof is applied at a rate from about 2 g acid equivalent (ae)/ha to about 300 gae/ha. In some embodiments, the bispyribac-sodium or carboxylic acid or ester thereof or other bispyribac salt is applied at a rate from about 3 gai/ha to about 80 gai/ha and the compound of formula (I) of salt or ester thereof is applied at a rate from about 4 g acid equivalent per hectare (gae/ha) to about 150 gae/ha. In some embodiments, the bispyribac-sodium or carboxylic acid or ester thereof or other bispyribac salt is applied at a rate from about 7 gai/ha to about 40 gai/ha and the compound of formula (I) of salt or ester thereof is applied at a rate from about 8.75 g acid equivalent per hectare (gae/ha) to about 70 gae/ha. In certain embodiments, the methods utilize the compound of formula (I), or its benzyl or n-butyl ester and bispyribac-sodium. In one embodiment, the methods utilize the compound of formula (I) and bispyribac-sodium, wherein the compound of formula (I) is applied at a rate of from about 8.75 g acid equivalent per hectare (gae/ha) to about 42.4 gae/ha, and bispyribac-sodium is applied at a rate of about 10 gai/ha to about 40 gai/ha. In one embodiment, the methods utilize the benzyl ester of the compound of formula (I) and bispyribac-sodium, wherein the benzyl ester of the compound of formula (I) is applied at a rate of from about 4.38 g acid equivalent per hectare (gae/ha) to about 70 gae/ha, and bispyribac-sodium is applied at a rate of about 7 gai/ha to about 40 gai/ha. In one embodiment, the methods utilize the n-butyl ester of the compound of formula (I) and bispyribac-sodium, wherein the n-butyl ester of the compound of formula (I) is applied at a rate of about 35 g acid equivalent per hectare (gae/ha) to about 70 gae/ha, and bispyribac-sodium is applied at a rate of about 40 gai/ha. In certain embodiments, the methods and compositions utilizing the compound of formula (I) or salt or ester thereof in combination with bispyribac-sodium or carboxylic acid or ester thereof or other bispyribac salt are used to control LEFCH, ECHCG, ECHOR, CYPRO, or SCPMA.

In certain embodiments of the compositions and methods described herein, the compound of formula (I) or salt or ester thereof is used in combination with pyribenzoxim or salt or ester thereof. With regard to the compositions, In some embodiments, the weight ratio of the compound of formula (I) or salt or ester thereof to pyribenzoxim or salt or ester thereof is within the range of from about 1:45 to about 10:1. In certain embodiments, the weight ratio of the compound of formula (I) or salt or ester thereof to pyribenzoxim or salt or ester thereof is within the range of from 1:12 to about 2:1. In certain embodiments, the compositions comprise the compound of formula (I) or its benzyl or n-butyl ester and pyribenzoxim. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 17 grams active ingredient per hectare (gai/ha) to about 360 gai/ha based on the total amount of active ingredients in the composition. In certain embodiments, the composition is applied at an application rate of from about 20 grams active ingredient per hectare (gai/ha) to about 200 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and pyribenzoxim, e.g., sequentially or simultaneously. In some embodiments, the pyribenzoxim or salt or ester thereof is applied at a rate from about 15 gai/ha to about 60 gai/ha and the compound of formula (I) of salt or ester thereof is applied at a rate from about 2 g acid equivalent (ae)/ha to about 300 gae/ha. In certain embodiments, the methods utilize the compound of formula (I) or its benzyl or n-butyl ester and pyribenzoxim.

In certain embodiments of the compositions and methods described herein, the compound of formula (I) or salt or ester thereof is used in combination with pyribenzoxim or salt or ester thereof. With regard to the compositions, In some embodiments, the weight ratio of the compound of formula (I) or salt or ester thereof to pyribenzoxim or salt or ester thereof is within the range of from about 1:45 to about 10:1. In certain embodiments, the weight ratio of the compound of formula (I) or salt or ester thereof to pyribenzoxim or salt or ester thereof is within the range of from 1:9 to about 1:4. In certain embodiments, the compositions comprise the compound of formula (I) or its benzyl or n-butyl ester and pyribenzoxim. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 17 grams active ingredient per hectare (gai/ha) to about 360 gai/ha based on the total amount of active ingredients in the composition. In certain embodiments, the composition is applied at an application rate of from about 20 grams active ingredient per hectare (gai/ha) to about 200 gai/ha based on the total amount of active ingredients in the composition. In further special embodiments, the composition is applied at an application rate of from about 78 grams active ingredient per hectare (gai/ha) to about 90 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and pyribenzoxim, e.g., sequentially or simultaneously. In some embodiments, the pyribenzoxim or salt or ester thereof is applied at a rate from about 15 gai/ha to about 60 gai/ha and the compound of formula (I) of salt or ester thereof is applied at a rate from about 2 g acid equivalent (ae)/ha to about 300 gae/ha. In certain embodiments, the methods utilize the compound of formula (I) or its benzyl or n-butyl ester and pyribenzoxim and are used to control ECHCG.

In certain embodiments of the compositions and methods described herein, the compound of formula (I) or salt or ester thereof is used in combination with pyriftalid or carboxylic acid or carboxylate salt thereof or other ester. With regard to the compositions, in some embodiments, the weight ratio of the compound of formula (I) or salt or ester thereof to pyriftalid or carboxylic acid or carboxylate salt thereof or other ester is within the range of from about 1:150 to about 3:1. In certain embodiments, the weight ratio of the compound of formula (I) or salt or ester thereof to pyriftalid or carboxylic acid or carboxylate salt thereof or other ester is within the range of from about 1:20 to about 1:1. In certain embodiments, the weight ratio of the compound of formula (I) or salt or ester thereof to pyriftalid or carboxylic acid or carboxylate salt thereof or other ester is within the range of from about 1:36 to about 2:1. In certain embodiments, the weight ratio of the compound of formula (I) or salt or ester thereof to pyriftalid or carboxylic acid or carboxylate salt thereof or other ester is within the range of from about 1:18 to about 1:1.4. In certain embodiments, the compositions provided herein comprise the compound of formula (I) or its benzyl or n-butyl ester and pyriftalid. In one embodiment, the composition comprises the compound of formula (I) and pyriftalid, wherein the weight ratio of the compound of formula (I) to pyriftalid is about 1:18 to about 1:1.4. In one embodiment, the composition comprises the benzyl ester of the compound of formula (I) and pyriftalid, wherein the weight ratio of the benzyl ester of the compound of formula (I) to pyriftalid is about 1:18 to about 1:2.6. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 102 grams active ingredient per hectare (gai/ha) to about 600 gai/ha based on the total amount of active ingredients in the composition. In certain embodiments, the composition is applied at an application rate of from about 49 grams active ingredient per hectare (gai/ha) to about 125 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and pyriftalid or carboxylic acid or carboxylate salt thereof or other ester, e.g., sequentially or simultaneously. In some embodiments, the pyriftalid or carboxylic acid or carboxylate salt thereof or other ester is applied at a rate from about 45 gai/ha to about 300 gai/ha and the compound of formula (I) of salt or ester thereof is applied at a rate from about 2 g acid equivalent (ae)/ha to about 300 gae/ha. In some embodiments, the pyriftalid or carboxylic acid or carboxylate salt thereof or other ester is applied at a rate from about 20 gai/ha to about 180 gai/ha and the compound of formula (I) of salt or ester thereof is applied at a rate from about 2 g acid equivalent per hectare (gae/ha) to about 70 gae/ha. In some embodiments, the pyriftalid or carboxylic acid or carboxylate salt thereof or other ester is applied at a rate from about 45 gai/ha to about 90 gai/ha and the compound of formula (I) of salt or ester thereof is applied at a rate from about 4.38 g acid equivalent per hectare (gae/ha) to about 35 gae/ha. In certain embodiments, the methods utilize the compound of formula (I), or its benzyl or n-butyl ester and pyriftalid. In one embodiment, the methods utilize the compound of formula (I) and pyriftalid, wherein the compound of formula (I) is applied at a rate of from about 4.38 g acid equivalent per hectare (gae/ha) to about 35 gae/ha, and pyriftalid is applied at a rate of about 45 gai/ha to about 90 gai/ha. In one embodiment, the methods utilize the benzyl ester of the compound of formula (I) and pyriftalid, wherein the benzyl ester of the compound of formula (I) is applied at a rate of from about 4.38 g acid equivalent per hectare (gae/ha) to about 17.5 gae/ha, and pyriftalid is applied at a rate of about 45 gai/ha to about 90 gai/ha. In certain embodiments, the methods and compositions utilizing the compound of formula (I) or salt or ester thereof in combination with pyriftalid or carboxylic acid or carboxylate salt thereof or other ester are used to control BRAPP, LEFCH, CYPRO, or FIMMI.

In certain embodiments of the compositions and methods described herein, the compound of formula (I) or salt or ester thereof is used in combination with pyriminobac-methyl or carboxylic acid or carboxylate salt thereof or other ester. With regard to the compositions, in some embodiments, the weight ratio of the compound of formula (I) or salt or ester thereof to pyriminobac-methyl or carboxylic acid or carboxylate salt thereof or other ester is within the range of from about 1:45 to about 27:1. In certain embodiments, the weight ratio of the compound of formula (I) or salt or ester thereof to pyriminobac-methyl or carboxylic acid or carboxylate salt thereof or other ester is within the range of from about 1:20 to about 3:1. In certain embodiments, the weight ratio of the compound of formula (I) or salt or ester thereof to pyriminobac-methyl or carboxylic acid or carboxylate salt thereof or other ester is within the range of from about 1:20 to about 4:1. In certain embodiments, the weight ratio of the compound of formula (I) or salt or ester thereof to pyriminobac-methyl or carboxylic acid or carboxylate salt thereof or other ester is within the range of from about 1:9 to about 1.6:1. In certain embodiments, the compositions provided herein comprise the compound of formula (I) or its benzyl or n-butyl ester and pyriminobac-methyl. In one embodiment, the composition comprises the compound of formula (I) and pyriminobac-methyl, wherein the weight ratio of the compound of formula (I) to pyriminobac-methyl is about 1:5 to about 1.6:1. In one embodiment, the composition comprises the benzyl ester of the compound of formula (I) and pyriminobac-methyl, wherein the weight ratio of the benzyl ester of the compound of formula (I) to pyriminobac-methyl is about 1:9 to about 1.6:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 13 grams active ingredient per hectare (gai/ha) to about 390 gai/ha based on the total amount of active ingredients in the composition. In certain embodiments, the composition is applied at an application rate of from about 15 grams active ingredient per hectare (gai/ha) to about 125 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and pyriminobac-methyl or carboxylic acid or carboxylate salt thereof or other ester, e.g., sequentially or simultaneously. In some embodiments, the pyriminobac-methyl or carboxylic acid or carboxylate salt thereof or other ester is applied at a rate from about 11 gr ai/ha to about 90 gai/ha and the compound of formula (I) of salt or ester thereof is applied at a rate from about 2 gai/ha to about 300 g acid equivalent (ae)/ha. In some embodiments, the pyriminobac-methyl or carboxylic acid or carboxylate salt thereof or other ester is applied at a rate from about 5 gai/ha to about 180 gai/ha and the compound of formula (I) of salt or ester thereof is applied at a rate from about 2 g acid equivalent per hectare (gae/ha) to about 140 gae/ha. In some embodiments, the pyriminobac-methyl or carboxylic acid or carboxylate salt thereof or other ester is applied at a rate from about 11.25 gai/ha to about 90 gai/ha and the compound of formula (I) of salt or ester thereof is applied at a rate from about 4.38 g acid equivalent per hectare (gae/ha) to about 70 gae/ha. In certain embodiments, the methods utilize the compound of formula (I), or its benzyl or n-butyl ester and pyriminobac-methyl. In one embodiment, the methods utilize the compound of formula (I) and pyriminobac-methyl, wherein the compound of formula (I) is applied at a rate of from about 4.38 g acid equivalent per hectare (gae/ha) to about 70 gae/ha, and pyriminobac-methyl is applied at a rate of about 11.25 gai/ha to about 90 gai/ha. In one embodiment, the methods utilize the benzyl ester of the compound of formula (I) and pyriminobac-methyl, wherein the benzyl ester of the compound of formula (I) is applied at a rate of from about 4.38 g acid equivalent per hectare (gae/ha) to about 35 gae/ha, and pyriminobac-methyl is applied at a rate of about 11.25 gai/ha to about 90 gai/ha. In certain embodiments, the methods and compositions utilizing the compound of formula (I) or salt or ester thereof in combination with pyriminobac-methyl or carboxylic acid or carboxylate salt thereof or other ester are used to control DIGSA, IPOHE, LEFCH, ECHCO, FIMMI, SCPMA, or CYPRO.

In certain embodiments of the compositions and methods described herein, the compound of formula (I) or salt or ester thereof is used in combination with pyrimisulfan or salt or ester thereof. With respect to the compositions, in some embodiments, the weight ratio of the compound of formula (I) or salt or ester thereof to pyrimisulfan or salt or ester thereof is within the range of from about 1:100 to about 30:1. In certain embodiments, the weight ratio of the compound of formula (I) or salt or ester thereof to pyrimisulfan or salt or ester thereof is within the range of from about 1:45 to about 10:1. In certain embodiments, the compositions provided herein comprise the compound of formula (I) or its benzyl or n-butyl ester and pyrimisulfan. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 12 grams active ingredient per hectare (gai/ha) to about 500 gai/ha based on the total amount of active ingredients in the composition. In certain embodiments, the composition is applied at an application rate of from about 15 grams active ingredient per hectare (gai/ha) to about 300 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and pyrimisulfan or salt or ester thereof, e.g., sequentially or simultaneously. In some embodiments, the pyrimisulfan or salt or ester thereof is applied at a rate from about 10 gai/ha to about 200 gai/ha and the compound of formula (I) of salt or ester thereof is applied at a rate from about 2 gae/ha to about 300 gae/ha. In certain embodiments, the methods utilize compound of formula (I) or its benzyl or n-butyl ester and pyrimisulfan.

The components of the mixtures described herein can be applied either separately or as part of a multipart herbicidal system.

The mixtures described herein can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the compositions and methods described herein include, but are not limited to: 4-CPA;

4-CPB; 4-CPP; 2,4-D; 2,4-D choline salt, 2,4-D esters and amines, 2,4-DB; 3,4-DA; 3,4-DB;

2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bialaphos, bicyclopyrone, bifenox, bilanafos, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone-ethyl, CDEA, CEPC, chlomethoxyfen, chloramben, chloranocryl, chlorazifop, chlorazine, chlorbromuron, chlorbufam, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, fluoroxypyr-meptyl, flurtamone, fluthiacet, fomesafen, foramsulfuron, fosamine, fumiclorac, furyloxyfen, glufosinate, glufosinate-ammonium, glufosinate-P-ammonium, glyphosate, halosafen, halauxifen, halauxifen-methyl, halosulfuron-methyl, haloxydine, haloxyfop-methyl, haloxyfop-P-methyl, hexachloroacetone, hexaflurate, hexazinone, imazamethabenz, imazamox, imazapic, imazapyr, imazaquin, imazosulfuron, imazethapyr, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, metsulfuron-methyl, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufen-ethyl, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen-ethyl, pyrasulfotole, pyrazogyl, pyrazolynate, pyrazosulfuron-ethyl, pyrazoxyfen, pyributicarb, pyriclor, pyridafol, pyridate, pyrimisulfan, pyrithiobac-sodium, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, SYN-523, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thifensulfurn-methyl, thiobencarb, tiocarbazil, tioclorim, topramezone, tralkoxydim, triafamone, tri-allate, triasulfuron, triaziflam, tribenuron, tribenuron-methyl, tricamba, triclopyr choline salt, triclopyr esters and salts, tridiphane, trietazine, trifloxysulfuron, trifluralin, triflusulfuron, trifop, trifopsime, trihydroxytriazine, trimeturon, tripropindan, tritac tritosulfuron, vernolate, xylachlor and salts, esters, optically active isomers and mixtures thereof.

The compositions and methods described herein, can further be used in conjunction with glyphosate, 5-enolpyruvylshikimate-3-phosphate (EPSP) synthase inhibitors, glufosinate, glutamine synthetase inhibitors, dicamba, phenoxy auxins, pyridyloxy auxins, synthetic auxins, auxin transport inhibitors, aryloxyphenoxypropionates, cyclohexanediones, phenylpyrazolines, acetyl CoA carboxylase (ACCase) inhibitors, imidazolinones, sulfonylureas, pyrimidinylthiobenzoates, triazolopyrimidines, sulfonylaminocarbonyltriazolinones, acetolactate synthase (ALS) or acetohydroxy acid synthase (AHAS) inhibitors, 4-hydroxyphenyl-pyruvate dioxygenase (HPPD) inhibitors, phytoene desaturase inhibitors, carotenoid biosynthesis inhibitors, protoporphyrinogen oxidase (PPO) inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil on glyphosate-tolerant, EPSP synthase inhibitor-tolerant, glufosinate-tolerant, glutamine synthetase inhibitor-tolerant, dicamba-tolerant, phenoxy auxin-tolerant, pyridyloxy auxin-tolerant, auxin-tolerant, auxin transport inhibitor-tolerant, aryloxyphenoxypropionate-tolerant, cyclohexanedione-tolerant, phenylpyrazoline-tolerant, ACCase-tolerant, imidazolinone-tolerant, sulfonylurea-tolerant, pyrimidinylthiobenzoate-tolerant, triazolopyrimidine-tolerant, sulfonylaminocarbonyltriazolinone-tolerant, ALS- or AHAS-tolerant, HPPD-tolerant, phytoene desaturase inhibitor-tolerant, carotenoid biosynthesis inhibitor tolerant, PPO-tolerant, cellulose biosynthesis inhibitor-tolerant, mitosis inhibitor-tolerant, microtubule inhibitor-tolerant, very long chain fatty acid inhibitor-tolerant, fatty acid and lipid biosynthesis inhibitor-tolerant, photosystem I inhibitor-tolerant, photosystem II inhibitor-tolerant, triazine-tolerant, bromoxynil-tolerant, and crops possessing multiple or stacked traits conferring tolerance to multiple chemistries and/or multiple modes of action via single and/or multiple resistance mechanisms. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation, as a tank mix or as a sequential application.

In some embodiments, the compositions described herein are employed in combination with one or more herbicide safeners, such as AD-67 (MON 4660), benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, jiecaowan, jiecaoxi, mefenpyr-diethyl, mephenate, naphthalic anhydride (NA), oxabetrinil, 829148 and N-phenyl-sulfonylbenzoic acid amides, to enhance their selectivity. In some embodiments, the safeners are employed in rice, cereal, corn, or maize settings. In some embodiments, the safener is cloquintocet or an ester or salt thereof. In certain embodiments, cloquintocet is utilized to antagonize harmful effects of the compositions on rice and cereals. In some embodiments, the safener is cloquintocet (mexyl).

In some embodiments, the compositions described herein are employed in combination with one or more plant growth regulators, such as 2,3,5-tri-iodobenzoic acid, IAA, IBA, naphthaleneacetamide, α-naphthaleneacetic acids, benzyladenine, 4-hydroxyphenethyl alcohol, kinetin, zeatin, endothal, ethephon, pentachlorophenol, thidiazuron, tribufos, aviglycine maleic hydrazide, gibberellins, gibberellic acid, abscisic acid, ancymidol, fosamine, glyphosine, isopyrimol, jasmonic acid, maleic hydrazide, mepiquat, 2,3,5-tri-iodobenzoic acid, morphactins, dichlorflurenol, flurprimidol, mefluidide, paclobutrazol, tetcyclacis, uniconazole, brassinolide, brassinolide-ethyl, cycloheximide, ethylene, methasulfocarb, prohexadione, triapenthenol and trinexapac.

In some embodiments, the plant growth regulators are employed in one or more crops or settings, such as rice, cereal crops, corn, maize, broadleaf crops, oilseed rape/canola, turf, pineapple, sugarcane, sunflower, pastures, grasslands, rangelands, fallowland, tree and vine orchards, plantation crops, vegetables, and non-crop (ornamentals) settings. In some embodiments, the plant growth regulator is mixed with the compound of formula (I), or mixed with the compound of formula (I) and a dimethoxy-pyrimidine to cause a preferentially advantageous effect on plants.

In some embodiments, compositions provided herein further comprise at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank mixed.

Suitable agricultural adjuvants and carriers include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In certain embodiments, water is the carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

In some embodiments, the compositions described herein further comprise one or more surface-active agents. In some embodiments, such surface-active agents are employed in both solid and liquid compositions, and in certain embodiments those designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkyl-naphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, and in certain embodiments, methyl esters.

In some embodiments, these materials, such as vegetable or seed oils and their esters, can be used interchangeably as an agricultural adjuvant, as a liquid carrier or as a surface active agent.

Other exemplary additives for use in the compositions provided herein include but are not limited to compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulators, fungicides, insecticides, and the like and can be formulated with liquid fertilizers or solid, particulate fertilizer carriers such as ammonium nitrate, urea and the like.

In some embodiments, the concentration of the active ingredients in the compositions described herein is from about 0.0005 to 98 percent by weight. In some embodiments, the concentration is from about 0.0006 to 90 percent by weight. In compositions designed to be employed as concentrates, the active ingredients, in certain embodiments, are present in a concentration from about 0.1 to 98 weight percent, and in certain embodiment's about 0.5 to 90 weight percent. Such compositions are, in certain embodiments, diluted with an inert carrier, such as water, before application. The diluted compositions usually applied to weeds or the locus of weeds contain, in certain embodiments, about 0.0006 to 3.0 weight percent active ingredient and in certain embodiments contain about 0.01 to 1.0 weight percent.

The present compositions can be applied to weeds or their locus by the use of conventional ground or aerial dusters, sprayers, and granule applicators, by addition to irrigation or paddy water, and by other conventional means known to those skilled in the art.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Results in Examples I and II are greenhouse trial results.

Example I

Evaluation of Postemergence Foliar-Applied Herbicidal Mixtures for Weed Control in Direct Seeded Rice Seeds or nutlets of the desired test plant species were planted in a soil matrix prepared by mixing a loam or sandy loam soil (e.g., 28.6 percent silt, 18.8 percent clay, and 52.6 percent sand, with a pH of about 5.8 and an organic matter content of about 1.8 percent) and calcareous grit in an 80 to 20 ratio. The soil matrix was contained in plastic pots with a volume of 1 quart and a surface area of 83.6 square centimeters ($cm^2$). When required to ensure good germination and healthy plants, a fungicide treatment and/or other chemical or physical treatment was applied. The plants were grown for 8-22 days in a greenhouse with an approximate 14 hr photoperiod which was maintained at about 29° C. during the day and 26° C. during the night. Nutrients (Peters Excel® 15-5-15 5-Ca 2-Mg and iron chelate) were applied in the irrigation solution as needed and water was added on a regular basis. Supplemental lighting was provided with overhead metal halide 1000-Watt lamps as necessary. The plants were employed for testing when they reached the first through fourth true leaf stage.

Treatments consisted of the acid or esters of 4-amino-3-chloro-5-fluoro-6-(4-chloro-2-fluoro-3-methoxy-phenyl) pyridine-2-carboxylic acid (Compound A), each formulated as an SC (suspension concentrate), and various herbicidal components alone and in combination. Forms of compound A were applied on an acid equivalent basis.

Forms of compound A (compound of formula I) tested include:

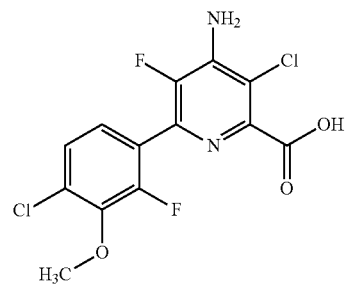

Compound A Acid

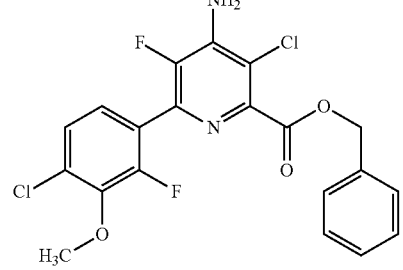

Compound A Benzyl Ester

Other herbicidal components were applied on an active ingredient basis and included the dimethoxy-pyrimidine acid acetolactate synthase (ALS)-inhibiting herbicides bispyribac-sodium formulated as Regiment® 80WP, pyribenzoxim (technical grade material), pyriminobac-methyl formulated as Hie-Clean® 1.2% GR dissolved in water, and pyriftalid (technical grade material).

Treatment requirements were calculated based upon the rates being tested, the concentration of active ingredient or acid equivalent in the formulation, and a 12 mL application volume at a rate of 187 L/ha.

For treatments comprised of formulated compounds, measured amounts of compounds were placed individually in 25 mL glass vials and diluted in a volume of 1.25% (v/v) Agri-Dex® crop oil concentrated to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of 10 mL of an aqueous mixture of 1.25% (v/v) crop oil concentrate so that the final spray solutions contained 1.25+/−0.005% (v/v) crop oil concentrate.

For treatments comprised of technical compounds, weighed amounts can be placed individually in 25 mL glass vials and dissolved in a volume of 97:3 v/v acetone/DMSO to obtain 12× stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of 10 mL of an aqueous mixture of 1.5% (v/v) crop oil concentrate so that the final spray solutions contain 1.25% (v/v) crop oil concentrate. When technical materials are used, the concentrated stock solutions can be added to the spray solutions so that the final acetone and DMSO concentrations of the application solutions are 16.2% and 0.5%, respectively.

For treatments comprised of formulated and technical compounds, weighed amounts of the technical materials were placed individually in 25 mL glass vials and dissolved in a volume of 97:3 v/v acetone/DMSO to obtain 12× stock solutions, and measured amounts of the formulated compounds were placed individually in 25 mL glass vials and diluted in a volume of 1.5% (v/v) crop oil concentrate or water to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of an appropriate amount of an aqueous mixture of 1.5% (v/v) crop oil concentrate so that the final spray solutions contained 1.25% (v/v) crop oil concentrate. As required, additional water and/or 97:3 v/v acetone/DMSO was added to individual application solutions so that the final acetone and DMSO concentrations of the application solutions being compared were 8.1% and 0.25%, respectively.

All stock solutions and applications solutions were visually inspected for compound compatibility prior to application. Spray solutions were applied to the plant material with an overhead Mandel track sprayer equipped with a 8002E nozzles calibrated to deliver 187 L/ha over an application area of 0.503 m² at a spray height of 18 to 20 inches (46 to 50 cm) above average plant canopy height. Control plants were sprayed in the same manner with the solvent blank.

The treated plants and control plants were placed in a greenhouse as described above and watered by sub-irrigation to prevent wash-off of the test compounds. After approximately 3 weeks, the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture.

B=observed efficacy of active ingredient B at the same concentration as used in the mixture.

The compounds tested, application rates employed, plant species tested, and results are given in Tables 1-6.

TABLE 1

Synergistic Activity of Foliar-Applied Compound A Benzyl Ester and Bispyribac-Sodium Herbicidal Compositions on Weed Control in a Rice Cropping System.

| Compound A Benzyl Ester | Bispyribac-Sodium | Visual Weed Control (%)-20 DAA LEFCH | |
|---|---|---|---|
| gae/ha | gai/ha | Obs | Exp |
| 8.75 | 0 | 10 | — |
| 17.5 | 0 | 20 | — |
| 0 | 7 | 0 | — |
| 0 | 14 | 0 | — |
| 8.75 | 7 | 25 | 10 |
| 17.5 | 7 | 40 | 20 |
| 8.75 | 14 | 25 | 10 |
| 17.5 | 14 | 60 | 20 |

TABLE 2

Synergistic Activity of Foliar-Applied Compound A Benzyl Ester and Pyribenzoxim Herbicidal Compositions on Weed Control in a Rice Cropping System.

| Compound A Benzyl Ester | Pyribenzoxim | Visual Weed Control (%)-20 DAA ECHCG | |
|---|---|---|---|
| gae/ha | gai/ha | Obs | Exp |
| 8 | 0 | 75 | — |
| 16 | 0 | 85 | — |
| 0 | 70 | 85 | — |
| 8 | 70 | 99 | 96 |
| 16 | 70 | 99 | 98 |

TABLE 3

Synergistic Activity of Foliar-Applied Compound A Acid and Pyriminobac-methyl Herbicidal Compositions on Weed Control in a Rice Cropping System.

| Compound A Acid | Pyriminobac-methyl | Visual Weed Control (%)-24 DAA | | | |
|---|---|---|---|---|---|
| | | DIGSA | | IPOHE | |
| gae/ha | gai/ha | Obs | Exp | Obs | Exp |
| 4.38 | 0 | 20 | — | 10 | — |
| 8.75 | 0 | 25 | — | 10 | — |
| 17.5 | 0 | 25 | — | 30 | — |
| 0 | 11.25 | 0 | — | 10 | — |
| 0 | 22.5 | 0 | — | 10 | — |

TABLE 3-continued

Synergistic Activity of Foliar-Applied Compound A Acid and
Pyriminobac-methyl Herbicidal Compositions on Weed Control
in a Rice Cropping System.

| 4.38 | 11.25 | 30 | 20 | 15 | 19 |
| 8.75 | 11.25 | 45 | 25 | 30 | 19 |
| 17.5 | 11.25 | 60 | 25 | 60 | 37 |
| 4.38 | 22.5 | 15 | 20 | 20 | 19 |
| 8.75 | 22.5 | 40 | 25 | 20 | 19 |
| 17.5 | 22.5 | 40 | 25 | 45 | 37 |

| Compound A Acid | Pyriminobac-methyl | Visual Weed Control (%)-24 DAA IPOHE | |
| --- | --- | --- | --- |
| gae/ha | gai/ha | Obs | Exp |
| 17.5 | 0 | 25 | — |
| 35 | 0 | 48 | — |
| 0 | 90 | 20 | — |
| 17.5 | 90 | 43 | 40 |
| 35 | 90 | 70 | 58 |

TABLE 4

Synergistic Activity of Foliar-Applied Compound A Benzyl Ester
and Pyriminobac-methyl Herbicidal Compositions
on Weed Control in a Rice Cropping System.

| Compound A Benzyl Ester | Pyriminobac-methyl | Visual Weed Control (%)-24 DAA | | | |
| --- | --- | --- | --- | --- | --- |
| | | LEFCH | | IPOHE | |
| gae/ha | gai/ha | Obs | Exp | Obs | Exp |
| 4.38 | 0 | 0 | — | 10 | — |
| 8.75 | 0 | 0 | — | 15 | — |
| 17.5 | 0 | 10 | — | 30 | — |
| 0 | 11.25 | 0 | — | 10 | — |
| 0 | 22.5 | 0 | — | 10 | — |
| 4.38 | 11.25 | 20 | 0 | 25 | 19 |
| 8.75 | 11.25 | 15 | 0 | 40 | 24 |
| 17.5 | 11.25 | 40 | 10 | 30 | 37 |
| 4.38 | 22.5 | 15 | 0 | 40 | 19 |
| 8.75 | 22.5 | 15 | 0 | 20 | 24 |
| 17.5 | 22.5 | 40 | 10 | 40 | 37 |

| Compound A Benzyl Ester | Pyriminobac-methyl | Visual Weed Control (%)-21 DAA IPOHE | |
| --- | --- | --- | --- |
| gae/ha | gai/ha | Obs | Exp |
| 17.5 | 0 | 43 | — |
| 0 | 90 | 20 | — |
| 17.5 | 90 | 65 | 54 |

TABLE 5

Synergistic Activity of Foliar-Applied Compound A Acid
and Pyriftalid Herbicidal Compositions on
Weed Control in a Rice Cropping System.

| Compound A Acid | Pyriftalid | Visual Weed Control (%)-22 DAA BRAPP | |
| --- | --- | --- | --- |
| gae/ha | gai/ha | Obs | Exp |
| 4.38 | 0 | 45 | — |
| 0 | 45 | 0 | — |
| 0 | 90 | 0 | — |
| 4.38 | 45 | 65 | 45 |
| 4.38 | 90 | 65 | 45 |

TABLE 6

Synergistic Activity of Foliar-Applied Compound A Benzyl
Ester and Pyriftalid Herbicidal Compositions
on Weed Control in a Rice Cropping System.

| Compound A Benzyl Ester | Pyriftalid | Visual Weed Control (%)-22 DAA LEFCH | |
| --- | --- | --- | --- |
| gae/ha | gai/ha | Obs | Exp |
| 17.5 | 0 | 25 | — |
| 0 | 45 | 0 | — |
| 0 | 90 | 0 | — |
| 17.5 | 45 | 40 | 25 |
| 17.5 | 90 | 35 | 25 |

BRAPP  *Brachiaria platyphylla* (Griseb.) Nash  signalgrass, broadleaf
DIGSA  *Digitaria sanguinalis* (L.) Scop.  crabgrass, large
ECHCG  *Echinochloa crusgalli* (L.) Beauv.  Barnyardgrass
IPOHE  *Ipomoea hederacea* Jacq.  morningglory, ivyleaf
LEFCH  *Leptochloa chinensis* (L.) Nees  sprangletop, Chinese
gae/ha = grams acid equivalent per hectare
gai/ha = grams active ingredient per hectare
Obs = observed value
Exp = expected value as calculated by Colby's equation
DAA = days after application Example II Evaluation of In-Water Applied Herbicidal Mixtures
for Weed Control in Transplanted Paddy Rice Weed seeds or nutlets of the desired test plant species were planted in puddled soil (mud) prepared by mixing a shredded, non-sterilized mineral soil (50.5 percent silt, 25.5 percent clay, and 24 percent sand, with a pH of about 7.6 and an organic matter content of about 2.9 percent) and water at a 1:1 volumetric ratio. The prepared mud was dispensed in 365 mL aliquots into 16-ounce (oz.) non-perforated plastic pots with a surface area of 86.59 square centimeters ($cm^2$) leaving a headspace of 3 centimeters (cm) in each pot. Mud was allowed to dry overnight prior to planting or transplanting. Rice seeds were planted in Sun Gro MetroMix® 306 planting mixture, which typically has a pH of 6.0 to 6.8 and an organic matter content of about 30 percent, in plastic plug trays. Seedlings at the second or third leaf stage of growth were transplanted into 860 mL of mud contained in 32-oz. non-perforated plastic pots with a surface area of 86.59 $cm^2$ 4 days prior to herbicide application. The paddy was created by filling the headspace of the pots with 2.5 to 3 cm of water. When required to ensure good germination and healthy plants, a fungicide treatment and/or other chemical or physical treatment was applied. The plants were grown for 4-22 days in a greenhouse with an approximate 14 hr photoperiod which was maintained at about 29'C during the day and 26° C. during the night. Nutrients were added as Osmocote® (19:6:

12, N:P:K+minor nutrients) at 2 g per 16-oz. pot and 4 g per 32-oz. pot. Water was added on a regular basis to maintain the paddy flood, and supplemental lighting was provided with overhead metal halide 1000-Watt lamps as necessary. The plants were employed for testing when they reached the first through fourth true leaf stage.

Treatments consisted of the acid or esters of 4-amino-3-chloro-5-fluoro-6-(4-chloro-2-fluoro-3-methoxy-phenyl) pyridine-2-carboxylic acid (compound A) each formulated as an SC and various herbicidal components alone and in combination. Forms of compound A were applied on an acid equivalent basis.

Forms of compound A (compound of formula I) tested include:

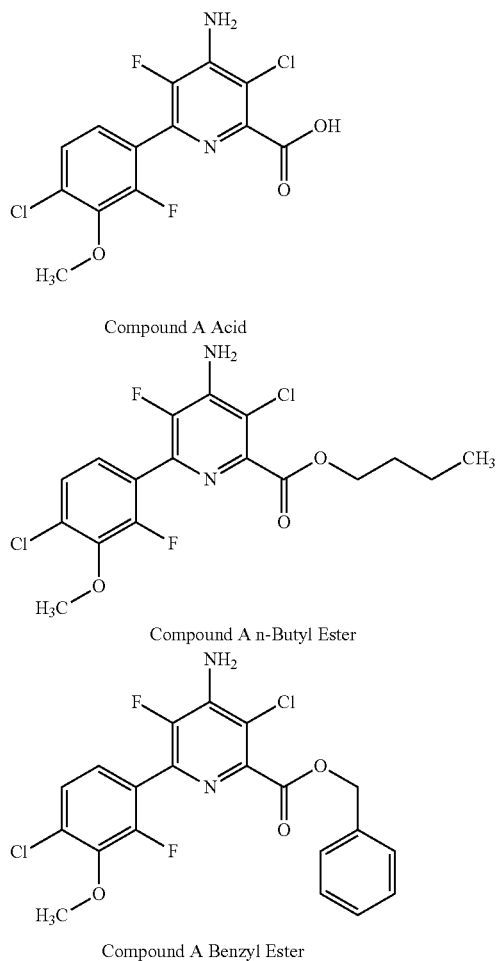

Compound A Acid

Compound A n-Butyl Ester

Compound A Benzyl Ester

Other herbicidal components were applied on an active ingredient basis and included the dimethoxy-pyrimidine acid acetolactate synthase (ALS)-inhibiting herbicides bispyribac-sodium formulated as Regiment® 80 WP, pyriminobac-methyl formulated as Hie Clean®, and pyriftalid (technical grade material).

Treatment requirements for each compound or herbicidal component were calculated based upon the rates being tested, the concentration of active ingredient or acid equivalent in the formulation, an application volume of 2 mL per component per pot, and an application area of 86.59 cm$^2$ per pot.

For formulated compounds, a measured amount was placed in an individual 100 or 200 mL glass vial and was dissolved in a volume of 1.25% (v/v) Agri-Dex® crop oil concentrate to obtain application solutions. If the test compound did not dissolve readily, the mixture was warmed and/or sonicated.

For technical grade compounds, a weighed amount was placed in an individual 100 to 200 mL glass vial and was dissolved in a volume of acetone to obtain concentrated stock solutions. If the test compound did not dissolve readily, the mixture was warmed and/or sonicated. The concentrated stock solutions obtained were diluted with an equivalent volume of an aqueous mixture containing 2.5% (v/v) crop oil concentrate so that the final application solutions contained 1.25% (v/v) crop oil concentrate.

Applications were made by injecting with a pipetter appropriate amounts of the application solutions, individually and sequentially, into the aqueous layer of the paddy.

Control plants were treated in the same manner with the solvent blank. Applications were made so that all treated plant material received the same concentrations of acetone and crop oil concentrate.

The treated plants and control plants were placed in a greenhouse as described above and water was added as needed to maintain a paddy flood. After approximately 3 weeks the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected} = A + B - (A \times B/100)$$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Tables 7-13.

TABLE 7

Synergistic Activity of In-Water Applications of Compound A Acid and Bispyribac-Sodium Herbicidal Compositions on Weed Control in a Rice Cropping System.

| Compound A Acid | Bispyribac sodium | Visual Weed Control (%) - 20 DAA | | | | | | | |
|---|---|---|---|---|---|---|---|---|---|
| | | ECHCG | | ECHOR | | LEFCH | | SCPMA | |
| gae/ha | gai/ha | Obs | Exp | Obs | Exp | Obs | Exp | Obs | Exp |
| 8.75 | 0 | 0 | — | | | | | | |
| 17.5 | 0 | 35 | — | | | | | | |
| 35 | 0 | 55 | — | | | | | | |

TABLE 7-continued

Synergistic Activity of In-Water Applications of Compound A Acid and Bispyribac-Sodium Herbicidal Compositions on Weed Control in a Rice Cropping System.

| | | | | | | | | | |
|---|---|---|---|---|---|---|---|---|---|
| 0 | 10 | 20 | — | | | | | | |
| 0 | 20 | 35 | — | | | | | | |
| 8.75 | 10 | 45 | 20 | | | | | | |
| 17.5 | 10 | 30 | 48 | | | | | | |
| 35 | 10 | 80 | 64 | | | | | | |
| 8.75 | 20 | 60 | 35 | | | | | | |
| 17.5 | 20 | 100 | 58 | | | | | | |
| 35 | 20 | 99 | 71 | | | | | | |
| 42.2 | 0 | 18 | — | 18 | — | 15 | — | 0 | — |
| 0 | 40 | 30 | — | 30 | — | 28 | — | 38 | — |
| 42.4 | 40 | 62 | 42 | 62 | 42 | 58 | 38 | 90 | 38 |

TABLE 8

Synergistic Activity of In-Water Applications of Compound A Benzyl Ester and Bispyribac-Sodium Herbicidal Compositions on Weed Control in a Rice Cropping System.

| Compound A Benzyl Ester | Bispyribac sodium | Visual Weed Control (%)-20 DAA CYPRO | |
|---|---|---|---|
| gae/ha | gai/ha | Obs | Exp |
| 4.38 | 0 | 50 | — |
| 0 | 10 | 0 | — |
| 0 | 20 | 0 | — |
| 4.38 | 10 | 70 | 50 |
| 4.38 | 20 | 95 | 50 |

| Compound A Benzyl Ester | Bispyribac sodium | Visual Weed Control (%)-20 DAA SCPMA | |
|---|---|---|---|
| gae/ha | gai/ha | Obs | Exp |
| 35 | 0 | 0 | — |
| 70 | 0 | 0 | — |
| 0 | 40 | 38 | — |
| 35 | 40 | 100 | 38 |
| 70 | 40 | 95 | 38 |

TABLE 9

Synergistic Activity of In-Water Applications of Compound A n-Butyl Ester and Bispyribac-Sodium Herbicidal Compositions on Weed Control in a Rice Cropping System.

| Compound A n-Butyl Ester | Bispyribac sodium | Visual Weed Control (%)-20 DAA ECHOR | |
|---|---|---|---|
| gae/ha | gai/ha | Obs | Exp |
| 35 | 0 | 35 | — |
| 70 | 0 | 40 | — |
| 0 | 40 | 30 | — |
| 35 | 40 | 68 | 55 |
| 70 | 40 | 100 | 58 |

| Compound A n-Butyl Ester | Bispyribac sodium | Visual Weed Control (%)-20 DAA SCPMA | |
|---|---|---|---|
| gae/ha | gai/ha | Obs | Exp |
| 70 | 0 | 0 | — |
| 0 | 40 | 38 | — |
| 70 | 40 | 75 | 38 |

TABLE 10

Synergistic Activity of In-Water Applications of Compound A Acid and Pyriminobac-methyl Herbicidal Compositions on Weed Control in a Rice Cropping System.

| Compound A Acid | Pyriminobac-methyl | Visual Weed Control (%)-21 DAA ECHCO | |
|---|---|---|---|
| gae/ha | gai/ha | Obs | Exp |
| 8.75 | 0 | 0 | — |
| 17.5 | 0 | 20 | — |
| 0 | 22.5 | 40 | — |
| 8.75 | 22.5 | 100 | 40 |
| 17.5 | 22.5 | 95 | 52 |

| Compound A Acid | Pyriminobac-methyl | Visual Weed Control (%)-21 DAA LEFCH | |
|---|---|---|---|
| gae/ha | gai/ha | Obs | Exp |
| 8.75 | 0 | 0 | — |
| 17.5 | 0 | 0 | — |
| 0 | 45 | 80 | — |
| 8.75 | 45 | 100 | 80 |
| 17.5 | 45 | 100 | 80 |

| Compound A Acid | Pyriminobac-methyl | Visual Weed Control (%)-21 DAA | | | |
|---|---|---|---|---|---|
| | | FIMMI | | SCPMA | |
| gae/ha | gai/ha | Obs | Exp | Obs | Exp |
| 8.75 | 0 | 50 | — | 0 | — |
| 17.5 | 0 | 85 | — | 0 | — |
| 35 | 0 | 85 | — | 0 | — |
| 0 | 22.5 | 0 | — | 0 | — |
| 0 | 45 | 0 | — | 0 | — |

TABLE 10-continued

Synergistic Activity of In-Water Applications of Compound A Acid and Pyriminobac-methyl Herbicidal Compositions on Weed Control in a Rice Cropping System.

| | | | | | |
|---|---|---|---|---|---|
| 8.75 | 22.5 | 80 | 50 | 0 | 0 |
| 17.5 | 22.5 | 100 | 85 | 30 | 0 |
| 35 | 22.5 | 100 | 85 | 100 | 0 |
| 8.75 | 45 | 85 | 50 | 95 | 0 |
| 17.5 | 45 | 100 | 85 | 30 | 0 |
| 35 | 45 | 100 | 85 | 95 | 0 |

| Compound A Acid | Pyriminobac-methyl | Visual Weed Control (%)-20 DAA SCPMA | |
|---|---|---|---|
| gae/ha | gai/ha | Obs | Exp |
| 35 | 0 | 0 | — |
| 70 | 0 | 0 | — |
| 0 | 90 | 43 | — |
| 35 | 90 | 53 | 43 |
| 70 | 90 | 85 | 43 |

TABLE 11

Synergistic Activity of In-Water Applications of Compound A Benzyl Ester and Pyriminobac-methyl Herbicidal Compositions on Weed Control in a Rice Cropping System.

| Compound A Benzyl Ester | Pyriminobac-methyl | Visual Weed Control (%)-21 DAA CYPRO | |
|---|---|---|---|
| gae/ha | gai/ha | Obs | Exp |
| 4.38 | 0 | 0 | — |
| 8.75 | 0 | 20 | — |
| 17.5 | 0 | 10 | — |
| 0 | 22.5 | 0 | — |
| 4.38 | 22.5 | 30 | 0 |
| 8.75 | 22.5 | 40 | 20 |
| 17.5 | 22.5 | 90 | 10 |

| Compound A Benzyl Ester | Pyriminobac-methyl | Visual Weed Control (%)-21 DAA SCPMA | |
|---|---|---|---|
| gae/ha | gai/ha | Obs | Exp |
| 4.38 | 0 | 0 | — |
| 8.75 | 0 | 0 | — |
| 0 | 22.5 | 0 | — |
| 0 | 45 | 0 | — |
| 4.38 | 22.5 | 60 | 0 |
| 8.75 | 22.5 | 20 | 0 |
| 4.38 | 45 | 20 | 0 |
| 8.75 | 45 | 20 | 0 |

| Compound A Benzyl Ester | Pyriminobac-methyl | Visual Weed Control (%)-20 DAA SCPMA | |
|---|---|---|---|
| gae/ha | gai/ha | Obs | Exp |
| 35 | 0 | 0 | — |
| 0 | 90 | 43 | — |
| 35 | 90 | 65 | 43 |

TABLE 12

Synergistic Activity of In-Water Applications of Compound A Acid and Pyriftalid Herbicidal Compositions on Weed Control in a Rice Cropping System.

| Compound A Acid | Pyriftalid | Visual Weed Control (%)-21 DAA CYPRO | |
|---|---|---|---|
| gae/ha | gai/ha | Obs | Exp |
| 8.75 | 0 | 30 | — |
| 17.5 | 0 | 40 | — |
| 35 | 0 | 70 | — |
| 0 | 45 | 0 | — |
| 0 | 90 | 0 | — |
| 8.75 | 45 | 85 | 30 |
| 17.5 | 45 | 20 | 40 |
| 35 | 45 | 80 | 70 |
| 8.75 | 90 | 50 | 30 |
| 17.5 | 90 | 50 | 40 |
| 35 | 90 | 85 | 70 |

TABLE 13

Synergistic Activity of In-Water Applications of Compound A Benzyl Ester and Pyriftalid Herbicidal Compositions on Weed Control in a Rice Cropping System.

| Compound A Benzyl Ester | Pyriftalid | Visual Weed Control (%)-21 DAA CYPRO | |
|---|---|---|---|
| gae/ha | gai/ha | Obs | Exp |
| 4.38 | 0 | 30 | — |
| 8.75 | 0 | 60 | — |
| 0 | 45 | 0 | — |
| 0 | 90 | 0 | — |
| 4.38 | 45 | 40 | 30 |
| 8.75 | 45 | 85 | 60 |
| 4.38 | 90 | 50 | 30 |
| 8.75 | 90 | 100 | 60 |

| Compound A Benzyl Ester | Pyriftalid | Visual Weed Control (%)-21 DAA FIMMI | |
|---|---|---|---|
| gae/ha | gai/ha | Obs | Exp |
| 4.38 | 0 | 20 | — |
| 0 | 45 | 50 | — |
| 0 | 90 | 30 | — |
| 4.38 | 45 | 100 | 60 |
| 4.38 | 90 | 90 | 44 |

| | | |
|---|---|---|
| CYPRO | *Cyperus rotundus* L. | nutsedge, purple |
| ECHCG | *Echinochloa crusgalli* (L.) Beauv. | barnyardgrass |
| ECHCO | *Echinochloa colona* (L.) Link | junglerice |
| FIMMI | *Fimbristylis miliacea* (L.) Vahl | fringerush, globe |
| LEFCH | *Leptochloa chinensis* (L.) Nees | sprangletop, Chinese |
| SCPMA | *Bolboschoenus maritimus* (L.) Palla | clubrush, sea | gae/ha = grams acid equivalent per hectare
gai/ha = grams active ingredient per hectare
Obs = observed value
Exp = expected value as calculated by Colby's equation
DAA = days after application

What is claimed is:

1. A herbicidal composition comprising a herbicidally effective amount of (a) a compound of the formula (I)

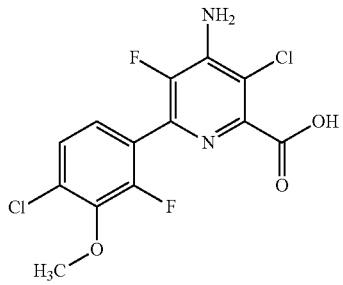

(I)

or an alkyl or benzyl ester, or an agriculturally acceptable salt of formula (I) and (b) a dimethoxy-pyrimidine acid, or salt or ester thereof selected from the group consisting of bispyribac-sodium, pyribenzoxim, pyriftalid, pyriminobac-methyl, or pyrimisulfan, wherein (a) and (b) are present in the composition in a ratio such that the composition exhibits herbicidal synergy.

2. The composition of claim 1, wherein (a) is a $C_{1-4}$ alkyl or benzyl ester of the compound of formula (I).

3. The composition of claim 2, wherein (a) is a benzyl ester of the compound of formula (I).

4. The composition of claim 1, wherein (a) is the compound of formula (I), which is the carboxylic acid.

5. The composition of claim 1, further comprising a herbicide safener, an adjuvant or a carrier.

6. The composition of claim 1, wherein the weight ratio of compound of formula (I) or agriculturally acceptable salt or ester thereof to bispyribac-sodium is from about 1:75 to about 43:1.

7. The composition of claim 1, wherein the weight ratio of the compound of formula (I) or agriculturally acceptable salt or ester thereof to pyribenzoxim is from about 1:45 to about 10:1.

8. The composition of claim 1, wherein the weight ratio of the compound of formula (I) or agriculturally acceptable salt or ester thereof to pyriftalid is from about 1:150 to about 3:1.

9. The composition of claim 1, wherein the weight ratio of the compound of formula (I) or agriculturally acceptable salt or ester thereof to pyriminobac-methyl is from about 1:45 to about 27:1.

10. The composition of claim 1, wherein the weight ratio of the compound of formula (I) or agriculturally acceptable salt or ester thereof to pyrimisulfan or agriculturally acceptable salt or ester thereof is from about 1:100 to about 30:1.

11. A method for controlling undesirable vegetation, comprising the step of:

contacting a plant, wherein the plant is undesirable vegetation or the locus thereof, or soil or water, wherein the soil or the water allows for the growth of the undesirable vegetation, with a herbicidally effective amount a composition comprising of (a) a compound of the formula (I)

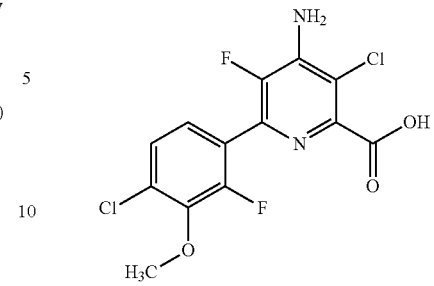

(I)

or an alkyl or benzyl ester, or an agriculturally acceptable salt of formula (I) and (b) a dimethoxy-pyrimidine acid, or a salt or ester thereof, selected from the group consisting of bispyribac-sodium, pyribenzoxim, pyriftalid, pyriminobac-methyl, or pyrimisulfan wherein (a) and (b) are present in the composition in a ratio such that the composition exhibits herbicidal synergy, and wherein the undesirable vegetation is controlled in direct-seeded, water-seeded, and transplanted rice, cereals, wheat, barley, oats, rye, sorghum, corn, or canola crops.

12. The composition comprising method of claim 11, wherein the (a) and (b) is applied to water.

13. The method of claim 11, wherein the water is part of a flooded rice paddy.

14. The composition comprising method of claim 11, wherein the (a) and (b) is applied pre-emergently and/or post-emergently to the undesirable vegetation in or the crop.

15. The method of claim 11, wherein the undesirable vegetation is controlled in glyphosate-, 5-enolpyruvylshikimate-3-phosphate synthase inhibitor-, glufosinate-, glutamine synthetase inhibitor-, dicamba-, phenoxy auxin-, pyridyloxy auxin-, synthetic auxin-, auxin transport inhibitor-, aryloxyphenoxypropionate-, cyclohexandione-, phenylpyrazoline-, acetyl CoA carboxylase inhibitor-, imidazolinone-, sulfonylurea-, pyrimidinylthiobenzoate, triazolopyrimidime-. sulfonylaminocarbonyltriazolinone-, acetolactate synthase or acetohydroxy acid synthease inhibitor-, 4-hydroxyphenylpyruvate dioxygenase inhibitor-, phytoene desaturase-, carotenoid biosynthesis inhibitor-, cellulose biosynthesis inhibitor-, mitosis inhibitor-, microtubule inhibitor-, very long chain fatty acid inhibitor-, fatty acid and lipid biosynthesis inhibitor-, photosystem 1 inhibitor, photosystem II inhibitor-, protoporphyrinogen oxidase inhibitor-, triazine-, or bromoxynil-tolerant crops.

16. The method of claim 11, wherein the undesirable vegetation comprises a herbicide resistant or tolerant weed.

17. The method of claim 11, wherein the undesirable vegetation is resistant or tolerant to acetolactate synthase inhibitors or acetohydroxy acid synthase photosystem II inhibitors, acetyl CoA carboxylase inhibitors, synthetic auxins, auxin transport inhibitors, photosystem I inhibitors, 5-enolpyruvylshikimate-3-phosphate synthase inhibitors, microtubule assembly inhibitors, fatty acid and lipid synthesis inhibitors, protoporphyrinogen oxidase inhibitors, carotenoid biosynthesis inhibitors, very long chain fatty acid inhibitors, phytoene desaturase inhibitors, glutamine synthetase inhibitors, 4-hydroxyphenyl-pyruvate-dioxygenase inhibitors, mitosis inhibitors, cellulose biosynthesis inhibitors, herbicides with multiple modes-of-action, quinclorac, arylaminopropionic acids, difenzoquat, endothall, or organoarsenicals.

* * * * *

UNITED STATES PATENT AND TRADEMARK OFFICE
CERTIFICATE OF CORRECTION

PATENT NO. : 8,871,680 B2
APPLICATION NO. : 13/833362
DATED : October 28, 2014
INVENTOR(S) : Carla N. Yerkes It is certified that error appears in the above-identified patent and that said Letters Patent is hereby corrected as shown below:

IN THE CLAIMS:

In Column 37, line 61, of claim 11, replace the text as follows:

"vegetation, with a herbicidally effective amount of a com-"

In Column 38, lines 24-25, of claim 12, replace the text as follows:

"The method of claim 11, wherein the composition comprising (a) and (b) is applied to water."

In Column 38, lines 28-29, of claim 14, replace the text as follows:

"The method of claim 11, wherein the composition comprising (a) and (b) is applied pre-emergently and/or"

Signed and Sealed this
Tenth Day of February, 2015

Michelle K. Lee
*Deputy Director of the United States Patent and Trademark Office*